(12) United States Patent
Schildkraut et al.

(10) Patent No.: US 12,383,220 B2
(45) Date of Patent: Aug. 12, 2025

(54) GEOMETRIC CALIBRATION MARKER DETECTION IN SPECTRAL TOMOSYNTHESIS SYSTEM

(71) Applicant: CARESTREAM DENTAL LLC, Atlanta, GA (US)

(72) Inventors: Jay S. Schildkraut, Rochester, NY (US); Jean-Marc Inglese, Bussy-Saint-Georges (FR); Subramanyan Krishnamoorthy, Penfield, NY (US)

( * ) Notice: Subject to any disclaimer, the term of this patent is extended or adjusted under 35 U.S.C. 154(b) by 346 days.

(21) Appl. No.: 17/635,937

(22) PCT Filed: Aug. 19, 2020

(86) PCT No.: PCT/US2020/046921
§ 371 (c)(1),
(2) Date: Feb. 16, 2022

(87) PCT Pub. No.: WO2021/034891
PCT Pub. Date: Feb. 25, 2021

(65) Prior Publication Data
US 2022/0330911 A1    Oct. 20, 2022

Related U.S. Application Data

(60) Provisional application No. 62/888,711, filed on Aug. 19, 2019.

(51) Int. Cl.
*A61B 6/00*  (2024.01)
*A61B 6/02*  (2006.01)
(Continued)

(52) U.S. Cl.
CPC ............. *A61B 6/584* (2013.01); *A61B 6/025* (2013.01); *A61B 6/4241* (2013.01); *A61B 6/425* (2013.01);
(Continued)

(58) Field of Classification Search
None
See application file for complete search history.

(56) References Cited

U.S. PATENT DOCUMENTS

2008/0186311 A1* 8/2008 Claus ................. A61B 6/032
                                              382/181
2013/0272494 A1* 10/2013 DeFreitas .......... A61B 6/025
                                              378/37

(Continued)

*Primary Examiner* — Hoon K Song

(57) ABSTRACT

A method for geometric calibration of a volume imaging apparatus disposes calibration phantom in a radiation path that includes a subject positioned between an x-ray source and a detector. The phantom has a number of radio-opaque markers formed of a marker material. In a repeated sequence, at each of a number of positional relationships of the x-ray source to the detector: 2D projection image data is acquired for the subject and the phantom, wherein the 2D projection image data distinguishes at least first and second x-ray energy distributions; source-to-detector geometry of the imaging apparatus is calculated, corresponding to the acquired 2D projection image data for the first and second x-ray energy distributions. The method reconstructs and displays a 3D volume image of the subject according to acquired anatomy image data from the subject and source-to-detector geometry within the 2D projection images.

20 Claims, 39 Drawing Sheets

(51) Int. Cl.
*A61B 6/42* (2024.01)
*A61B 6/46* (2024.01)
*A61B 6/51* (2024.01)
*A61B 6/58* (2024.01)
*A61B 90/00* (2016.01)

(52) U.S. Cl.
CPC ............... *A61B 6/466* (2013.01); *A61B 6/51* (2024.01); *A61B 6/5252* (2013.01); *A61B 2090/3966* (2016.02)

(56) References Cited

U.S. PATENT DOCUMENTS

| | | | |
|---|---|---|---|
| 2018/0328865 A1* | 11/2018 | Engel | A61B 6/482 |
| 2020/0000426 A1* | 1/2020 | Simon | A61B 6/4405 |

* cited by examiner

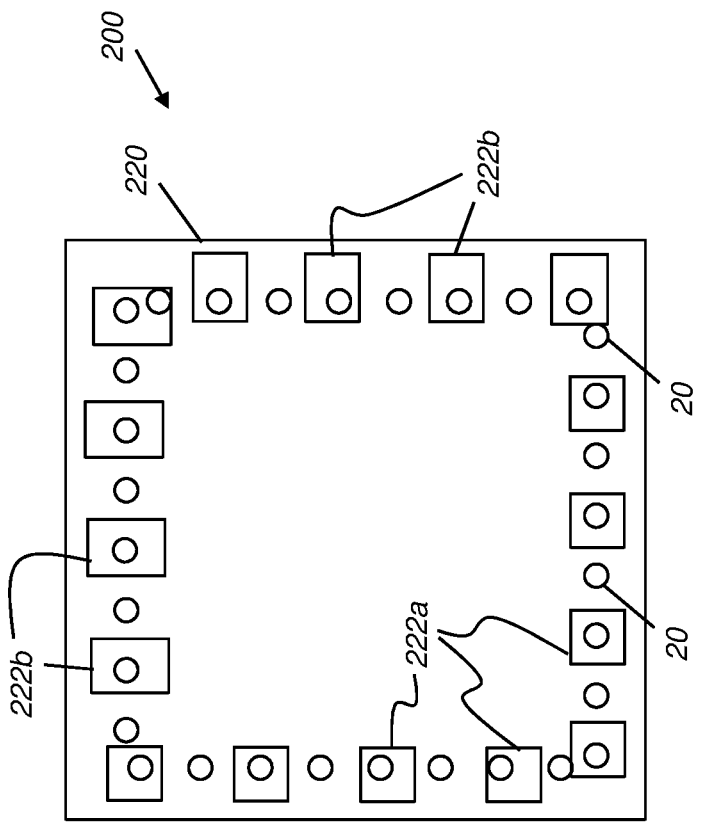
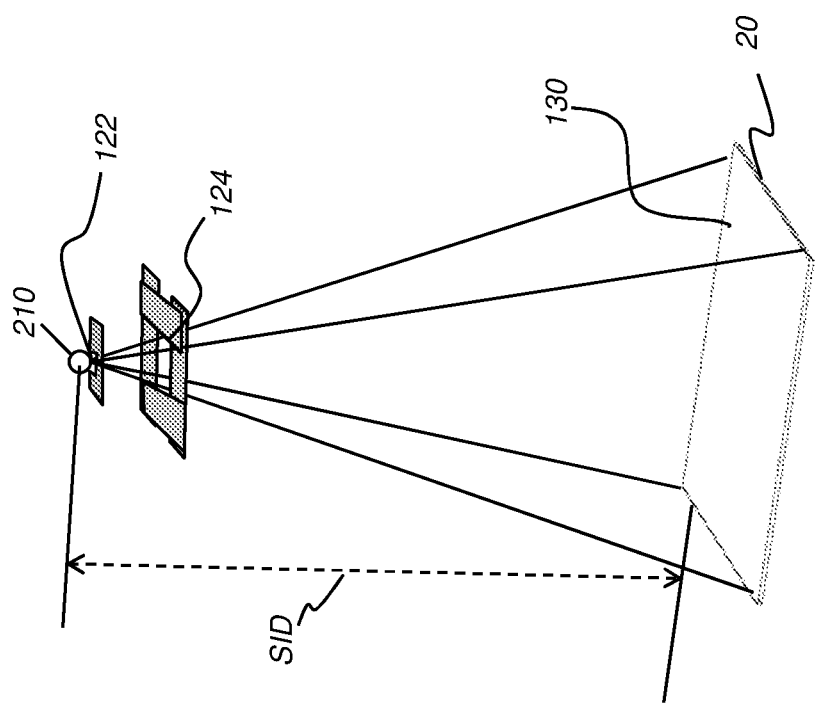
*FIG. 8B*
*FIG. 8A*

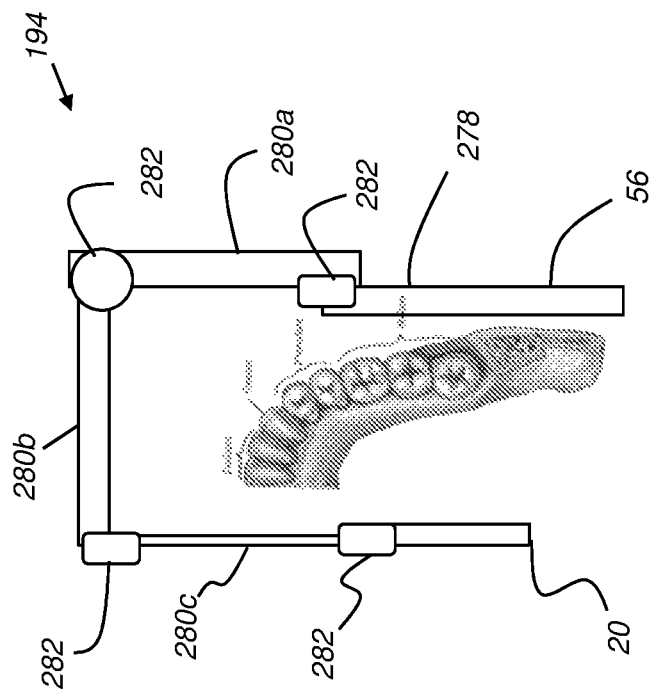

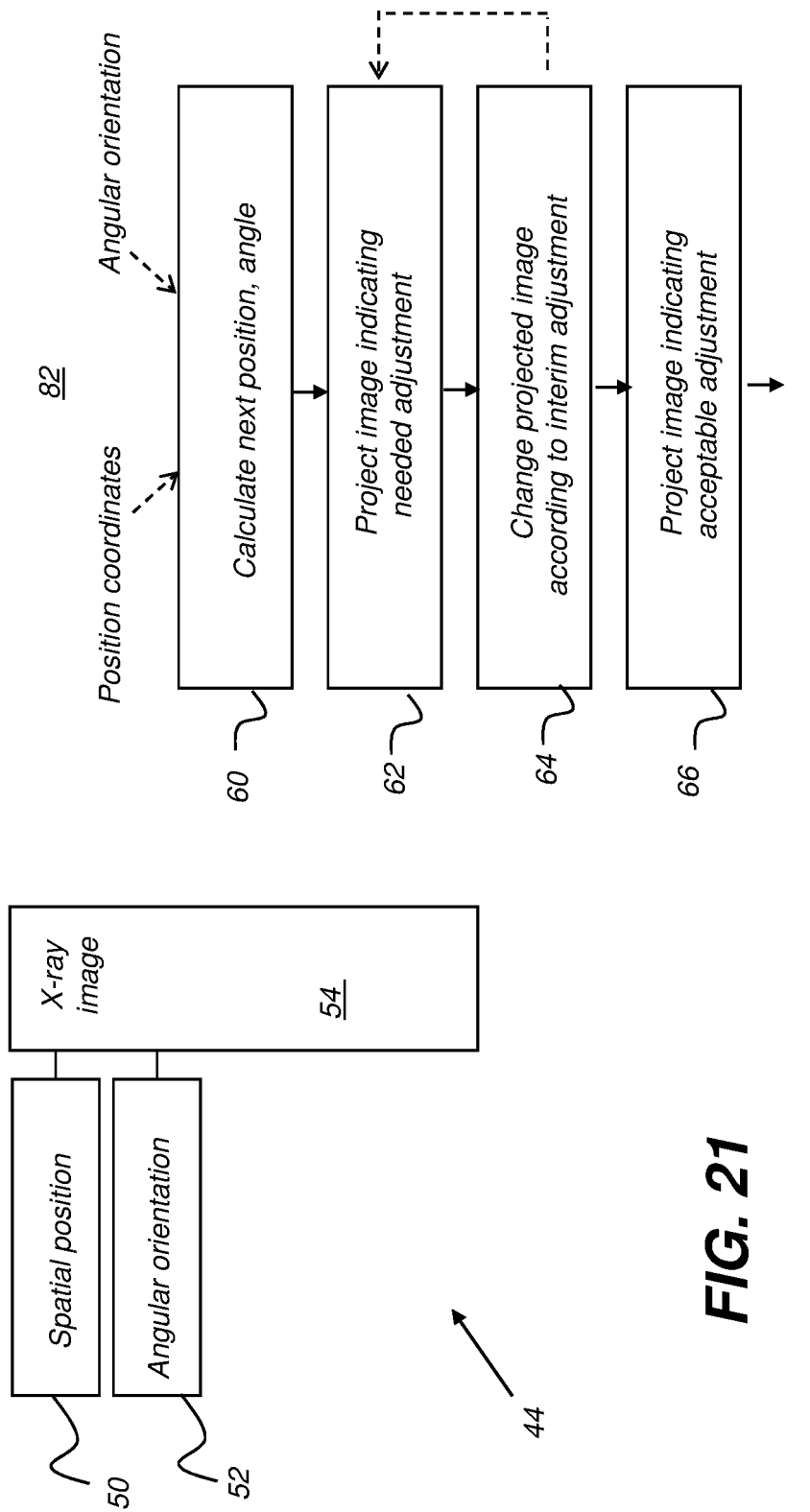

GEOMETRIC CALIBRATION MARKER DETECTION IN SPECTRAL TOMOSYNTHESIS SYSTEM

TECHNICAL FIELD

The disclosure relates generally to 3D volume radiographic imaging and more particularly relates to methods and apparatus for automatic detection of calibration markers used in tomosynthesis imaging.

BACKGROUND

A 3-dimensional (3D) or volume x-ray image can be of significant value for diagnosis and treatment of teeth and supporting structures. A volume x-ray image for this purpose is formed by combining image data from two or more individual 2D projection images, obtained within a short time of each other and with a well-defined angular and positional geometry between each projection image and the subject tooth and between each projection image and the other projection images.

Cone-Beam Computed Tomography (CBCT) is one established method for obtaining a volume image of dental structures from multiple projection images. In CBCT imaging, an image detector and a radiation source orbit a subject and obtain a series of x-ray projection images at small angular increments. The information obtained is then used to synthesize a volume image that faithfully represents the imaged subject to within the available resolution of the system, so that the volume image that is formed can then be viewed from any number of angles. Commercially available CBCT apparatus for dental applications include the CS 8100 3D System from Carestream Dental LLC, Atlanta, Geogia.

While CBCT imaging is a powerful diagnostic tool, there can be cases where, even though volume imaging is beneficial, the full-fledged capability of CBCT imaging is not needed. This has been acknowledged, for example, in the disclosures of U.S. Patent Application Publication No. 2007/0127801 entitled "Method for Limited Angle Tomography" by Kalke and U.S. Pat. No. 7,269,241 entitled "Method and Arrangement for Medical X-ray Imaging and Reconstruction from Sparse Data" issued to Siltanen et al. For some types of volume imaging, such as for use in guiding implant placement, for example, a rudimentary volume imaging capability would be useful. Volume imaging can also help to avoid superposition anomalies between adjacent dental structures. For uses such as these, numerous x-ray projection images, such as those provided from a CBCT system would not be required. Instead, sufficient volume information can be obtained using a smaller number of x-ray images, provided a spatial coordinate reference between images is maintained.

As a general principle, it would be advantageous to obtain the minimum number of x-ray exposures needed in order to generate the volume diagnostic data. A complete CBCT series of projection images acquired over a 180-degree orbit requires higher cumulative radiation dosage than does a partial series that is either taken over a smaller range of angles or uses fewer projection images taken at increased relative angular increments. Thus, the methods taught in the Kalke and Siltanen et al. disclosures can help to reduce patient exposure where full CBCT imaging is not needed.

Tomosynthesis, sometimes referred to as "2.5D imaging" appears to offer the dental practitioner a number of advantages over conventional 2D radiography and 3D tomography imaging, such as CBCT imaging, of intraoral features. In tomosynthesis, as with other volume imaging approaches, a limited number of 2D projection images are obtained in sequence, with each image frame shifted in terms of relative angle from the previously acquired image frame. Reconstruction techniques can then be used to form a volume image of sufficient depth and resolution for a number of diagnosis and assessment functions. This gives tomosynthesis some of the benefits of full-scale tomography imaging for providing volume data, but at lower dose than tomography requires.

Tomosynthesis imaging employs incremental geometric change of the relative radiation source angle, at each image, with respect to the detector surface. Conventional tomosynthesis systems, such as those used for mammography, for example, have mechanical coupling that provides inherent control of source position relative to detector. This mechanical coupling inherently achieves geometric calibration, with alignment that applies from one imaging exam to the next.

Fixed mechanical coupling of the detector with respect to the source is not always possible. With some types of tomosynthesis imaging, the detector and source are uncoupled, requiring some method for providing geometric alignment and calibration.

It should be noted that alignment and geometric calibration are related, but not identical. Alignment relates to beam direction and occurs prior to imaging. Geometric calibration can be provided following imaging, such as by processing each individual acquired image, as described herein.

Proper alignment of source to detector positions the x-ray energy so that the x-ray beam is incident only within the boundaries of the detector. Once alignment is achieved, correct geometric calibration data obtained from image content then defines the relative spatial positions of the x-ray source and detector for each successive projection image, so that reconstruction techniques can accurately generate volume 3D image data from the acquired 2D projection images.

For most dental applications, the intraoral detector, deployed behind the patient's teeth with respect to the x-ray source, is largely hidden from view and must be flexibly positionable at various locations within the mouth, frustrating attempts at straightforward source-to-detector alignment and complicating the task of geometric calibration. Not only should the system be able to positively identify the boundary geometry of the detector outline by proper alignment, but the relative position of the x-ray source to the detector must be known, using geometric calibration, in order to allow accurate 3D volume reconstruction from the 2D projection images.

The use of radio-opaque markers, positioned in the path of the x-ray beam, provides a workable solution for geometric calibration, but presents significant drawbacks. The radio-opaque characteristic of markers obscures portions of the underlying anatomy, which can potentially compromise the quality of the acquired image for diagnostic purposes. Attempts to diminish this problem by reducing marker size or density can make the markers difficult to distinguish from the anatomy and complicate or jeopardize accurate geometric calibration.

Although a number of solutions have been proposed for providing intraoral tomosynthesis, there remain considerable areas for improvement in making tomosynthesis technology suitable for the dental practitioner.

Thus, it can be appreciated that there is a need for improvement in apparatus and methods that provide accurate geometric calibration for intraoral tomosynthesis systems in which the detector and radiation source are not mechanically coupled.

SUMMARY

Broadly described and in accordance with example embodiments described herein, the present invention comprises apparatuses and methods for generating a volume image from a small number of radiographic images obtained by an intraoral imaging detector. More particularly, the present invention comprises apparatuses and methods for geometric calibration of a volume imaging apparatus in which the detector and source are not mechanically coupled. Advantageously, the present invention addresses problems introduced in the tradeoff between accurate marker detection and impact on image quality. Notwithstanding anything to the contrary herein, the present invention is defined by the appended claims.

According to one aspect of the disclosure, a method is provided for geometric calibration of a volume imaging apparatus, the method comprising:

(a) disposing a calibration phantom in a radiation path that includes a subject positioned between an x-ray source and a detector, wherein the phantom has a plurality of radio-opaque markers formed of a marker material;

(b) in a repeated sequence, at each of a plurality of relative positional relationships of the x-ray source to the detector:

(i) acquiring 2D projection image data for the subject and the phantom, wherein the 2D projection image data distinguishes at least first and second x-ray energy distributions;

(ii) calculating source-to-detector geometry of the imaging apparatus corresponding to the acquired 2D projection image data for the first and second x-ray energy distributions; and (c) reconstructing and displaying a 3D volume image of the subject according to acquired anatomy image data from the subject and calculated source-to-detector geometry within the plurality of 2D projection images.

The present invention and the example embodiments thereof described herein address, in whole or at least in part, the problems, deficiencies, and shortcomings of the related art. In addition, the present invention and such example embodiments provide various advantages and benefits described herein. Other advantages and benefits inherently achieved by the disclosed apparatuses and methods may occur or become apparent to those skilled in the art.

BRIEF DESCRIPTION OF THE DRAWINGS

The foregoing and other objects, features, and advantages of the invention will be apparent from the following more particular description of the example embodiments of the invention, as illustrated in the accompanying drawings. The elements of the drawings are not necessarily to scale relative to each other.

FIG. 8A is a bottom view that shows a radiation source assembly with collimation in a substantially square arrangement.

FIG. 8B is a bottom view showing a collimator plate assembly with apertures of different aspect ratios.

FIG. 10C is a top view schematic that shows a frame having multiple articulated sections at each adjustable joint for reporting sensed extension and rotation data.

FIG. 21 is a block diagram showing spatial position and angular orientation information associated with the image data.

FIG. 22 is a logic flow diagram that shows system activity in preparation for each image capture in a sequence.

DETAILED DESCRIPTION OF EXAMPLE EMBODIMENTS

Figure 1:
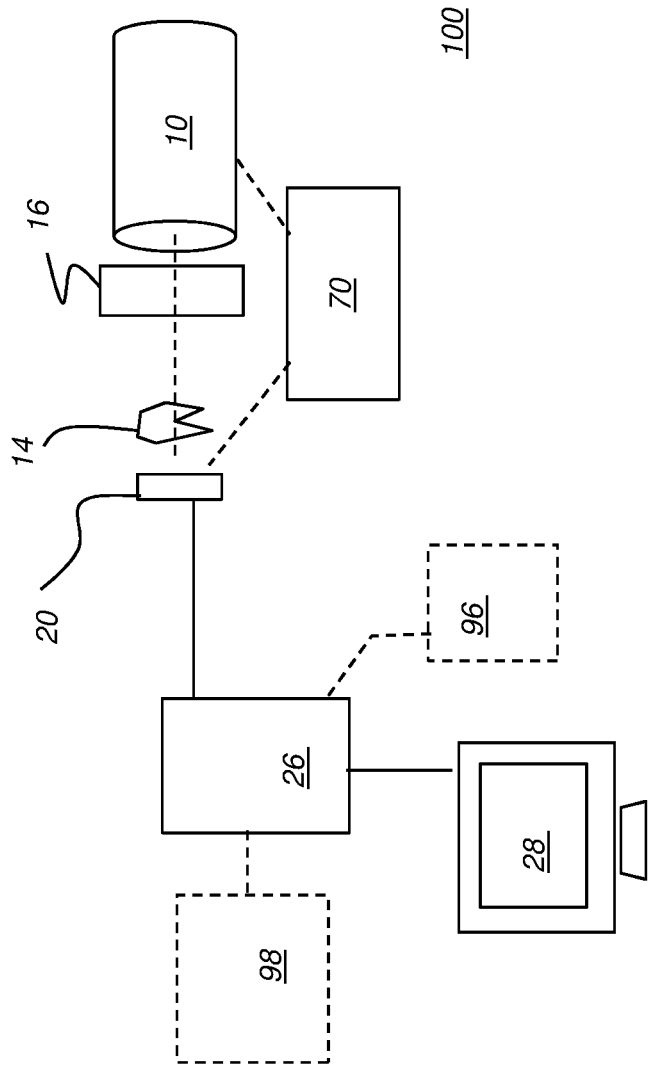
FIG. 1 is a schematic diagram showing components of a chairside tomosynthesis imaging apparatus according to an example embodiment according to the application.

The following is a detailed description of example embodiments, reference being made to the drawings in which the same reference numerals identify the same elements of structure or same steps of a method, as the case may be, in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

As used herein, the term "energizable" relates to a device or set of components that perform an indicated function upon receiving power and, optionally, upon receiving an enabling signal.

In the context of the present disclosure, the terms "viewer", "operator", and "user" are considered to be equivalent and refer to the viewing practitioner, technician, or other person who views and manipulates an image, such as a dental image, on a display monitor. An "operator instruction" or "viewer instruction" is obtained from explicit commands entered by the viewer, such as by clicking a button on a camera or by using a computer mouse or by touch screen or keyboard entry.

In the context of the present disclosure, the phrase "in signal communication" indicates that two or more devices and/or components are capable of communicating with each other via signals that travel over some type of signal path. Signal communication may be wired or wireless. The signals may be communication, power, data, or energy signals. The signal paths may include physical, electrical, magnetic, electromagnetic, optical, wired, and/or wireless connections between the first device and/or component and second device and/or component. The signal paths may also include additional devices and/or components between the first device and/or component and second device and/or component.

The term "subject" refers to the tooth or other portion of a patient that is being imaged and, in optical terms, can be considered equivalent to the "object" of the corresponding imaging system.

In the present disclosure, the term "detector" refers to the element that is placed in the patient's mouth, receives radiation, and provides the image content. Such a detector is a digital detector that provides the x-ray image data directly to an imaging system.

In the context of the present disclosure, the terms "pixel" and "voxel" may be used interchangeably to describe an individual digital image data element, that is, a single value representing a measured image signal intensity. Conventionally an individual digital image data element is referred to as a voxel for 3-dimensional volume images and a pixel for 2-dimensional images. Volume images, such as those from CT or CBCT apparatus, are formed by obtaining multiple 2D images of pixels, taken at different relative angles, then combining the image data to form corresponding 3D voxels. For the purposes of the description herein, the terms voxel and pixel can generally be considered equivalent, describing an image elemental datum that is capable of having a range of numerical values. Voxels and pixels have the attributes of both spatial location and image data code value.

Planes can be considered "in parallel" if they are parallel to within no more than 12 degrees in any direction.

Although particularly described with respect to tomosynthesis imaging, an embodiment of the present disclosure can also be used with other types of volume imaging apparatus, such as with a computed tomography (CT) imaging system that generates a larger number of 2D projection images used for reconstruction of the 3D volume, such as a CBCT imaging apparatus, for example.

FIG. 1 is a schematic diagram showing components of an example chairside tomosynthesis imaging apparatus 100 according to certain example method and/or apparatus embodiments of the present disclosure. An x-ray source 10 directs radiant energy through a subject tooth 14 or other feature toward an intraoral detector 20, at each of a plurality of positional relationships of the x-ray source relative to the detector. Each positional relationship can be considered as a pairing of respective spatial coordinates of source and detector. A collimator 16 conditions the angular extent of source 10 radiation so that the exposure is constrained to within the region of interest. An alignment apparatus 70 senses and optionally controls the alignment of the radiation field from source 10 and through collimator 16 to provide radiation over the region of interest. Intraoral detector 20 is in signal communication with a control logic processor 26 that acquires and processes the image content to provide a tomosynthesis image on a display 28. Tomosynthesis imaging requires a changing relative angle or, more generally, positional relationship of the source 10 to the detector 20, as described in more detail herein. Control logic processor 26 provides the control required for tomosynthesis image acquisition.

Tomosynthesis imaging requires that the components shown in FIG. 1 acquire two or more 2D projection images of the region of interest, such as images of one or more adjacent teeth, for example. The generated image content includes some amount of contour and depth information, but not the more geometrically complete 3D image volume data obtained from tomography, such as from CBCT systems.

The tomosynthesis data provides a measure of depth information without full volume image content. Tomosynthesis allows generation of slices into the imaged object, wherein the slices are at different depths.

Reflectance Image Acquisition

An optional reflectance imaging apparatus 96 can also be provided as part of some example chairside oral imaging method and/or apparatus embodiments, such as for providing more accurate positioning information for the detector 20 placed within the mouth of the patient. Imaging apparatus 96 can provide contour imaging, such as by projection of a structured light pattern onto the intraoral feature of interest. Contour information is then processed in order to generate a 3D mesh showing surface features. For this purpose, the reflectance imaging camera serves as an optical scanner. Alternately, imaging apparatus 96 can be a 2D camera for obtaining one or more monochromatic or color images from and around the region of interest.

Reflectance imaging can be used, for example, to determine head size and/or orientation. Acquired reflectance images can also serve as an aid to detecting patient motion during tomosynthesis and/or other radiological image acquisition. A contour imaging camera image, such as provided by a CS3600 intraoral scanner from Carestream Dental LLC, can provide more information than 2D reflectance images for guiding and/or correcting the volume reconstruction processing used in tomosynthesis and for motion detection during the tomosynthesis exam.

An optional ultrasound imaging apparatus 98 can similarly be provided as a support system for chairside oral imaging apparatus 100.

According to an alternate example embodiment according to the application, a full-mouth scanning apparatus works in conjunction with the radiographic imaging system. This enables the simultaneous acquisition of both radiographic and reflectance images, for example, which can be useful for subsequent reconstruction processing. The reflectance and tomosynthesis image content can be fused together to show some depth information with reference to highly accurate surface contour information.

Types of imaging apparatus that acquire depth-resolved image content, such as optical coherence tomography (OCT) and ultrasound imaging systems, obtain from captured reflectance signals not only surface contour information, but also potentially provide some amount of additional information for characterization of tissue and features detected, up to some depth below the surface. This type of depth-resolved image content can be a more useful aid to support and validate positioning of the tomosynthesis acquisitions as well as to help identify and report or compensate for detected movement of the patient during the imaging session. There can be supportive information obtained by depth-resolved imaging apparatus for features just beneath the surface, for example, that can be more useful for positioning guidance and verification than is available when only using surface contour imaging content.

Radiation Source

According to example method and/or apparatus embodiments of the present disclosure, the x-ray source 10 is a Spindt-type field emitter (including carbon nanotube-based field emitters), providing radiant energy from a number of distributed x-ray sources. The x-ray sources can be, for example, a distributed array of Spindt-type field emitters, which can be peripherally arranged about a central thermionic source. The x-ray sources are stationary or relatively fixed in position with respect to each other within the array; the array itself moves as a single unit. This type of x-ray source is capable of rapid on/off switching on the order of microseconds.

Other suitable x-ray sources can include paired pulsed conventional fluoro-capable thermionic sources in an array, where the sources are spatially separated. These options provide sufficient x-ray fluence with short exposure times and simultaneously allow exposure sequences without overheating.

A Spindt-type field emitter based x-ray source has one or more cathodes within a vacuum chamber, wherein each cathode is formed from a large number of individual Spindt-type field emitters that, given excitation current, provide electrons that are then accelerated toward one or more anodes in the chamber.

Alternately, the x-ray source can be a more conventional thermionic source, coupled with a transport apparatus that provides the needed energy to move the x-ray source along a linear or non-linear (e.g., curved) travel path that can be segmented or continuous for directing radiation toward the subject.

According to an example embodiment according to the application, the same x-ray source can be used in any of a set of modes for conventional radiography or 3D imaging. Thus, the same radiation imaging apparatus can be used for acquiring single-shot radiographic images, or for acquiring and processing projection images for tomography including CBCT, tomosynthesis, or for fluoroscopy or radioscopy imaging, as described in more detail herein.

Generator

The radiation generator that is part of the x-ray source can provide pulsed or continuous operation. The generator can provide a single pulse or a series of pulses, with pulse widths varied in order to provide suitable exposure conditions for particular features.

Imaging Detector

The imaging detector in example method and/or apparatus embodiments is a small, intraoral digital radiography (DR) detector that acquires image data at a rate sufficient for tomosynthesis imaging. The imaging detector can be any suitable shape and can be rigid or flexible.

Signal communication with the imaging detector can be wired or wireless. The image detector can receive power from a cable or can have an on-board rechargeable battery.

In order to meet the requirements of tomosynthesis imaging, the intraoral detector has a fast response time, with an image acquisition rate sufficient for tomosynthesis acquisition, acquiring at least about 2 frames per second (fps), at least 5 fps, or at least 10 fps.

As noted previously in the background section, both source-to-detector alignment and geometric calibration data for source position relative to the detector are used to acquire and process the 2D projection images obtained by the tomosynthesis imaging apparatus. Subsequent description outlines a number of solutions to the alignment problem and apparatus and methods for obtaining the geometric calibration data that is used for accurate tomosynthesis or tomography reconstruction.

Particular embodiments of the present disclosure address the problem of geometric calibration using spectral detection capabilities of tomosynthesis imaging apparatus 100. For this purpose, spectral characteristics of the tomosynthesis imaging apparatus are used, as described in more detail subsequently.

One aspect of tomosynthesis imaging that can be used for obtaining spectral information in the acquired image content relates to photon-counting x-ray detectors. Some of the advantages of the photon counting detection for imaging compared to conventional detectors that employ energy integration detection include: (i) reduction of electrical noise and improvement of the signal-to-noise ratio; and (ii) improvement of image contrast, such as adjusting weighting factors for images acquired with energy binning. Photon counting tomosynthesis can thus provide improved diagnostic accuracy. Embodiments of the present disclosure can take further advantage of photon counting to acquire spectral information related to geometric calibration.

In photon counting, each incoming photon generates a charge, and each charge event is recorded. The actual count of photons, or a value correspondingly computed according to the count, is provided as the image data for each pixel. Advantageously, photon counting has high immunity to noise, provided that pulse strength exceeds background noise levels.

Figure 2A:
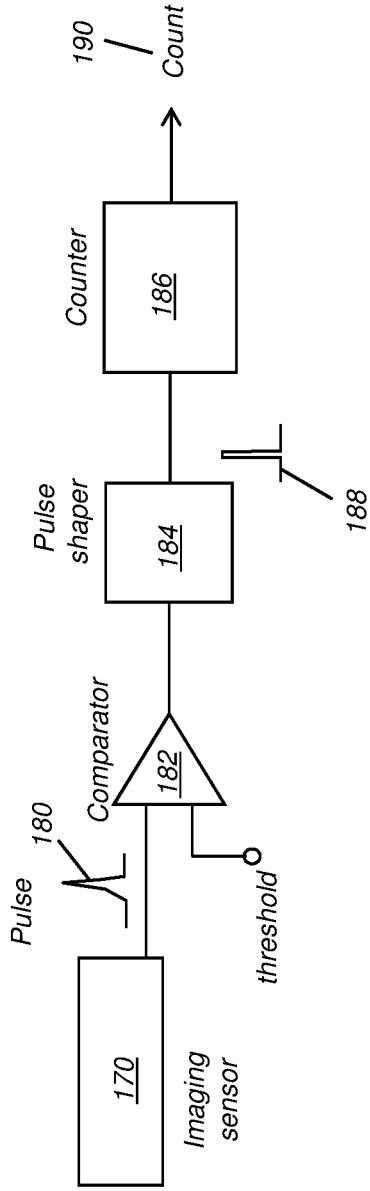
FIG. 2A is a schematic diagram that shows the photon-counting sequence.

FIG. 2A shows the photon-counting sequence in schematic form. An incoming photon generates a pulse 180 at a given energy level, corresponding to its frequency (or, inversely corresponding to its wavelength). The pulse 180 energy is compared against a threshold value at a comparator 182 and shaped in a pulse shaper 184 to form a shaped pulse 188. A counter 186 then records the pulse event and provides a digital output, a pulse count value 190. A separate pulse count value 190 is obtained for each pixel element in imaging sensor 170 that is used for detector 20. The threshold value can be adjustable or selectable from a range of values, depending on the photon energies of interest. Photon counting x-ray detectors provide suitable performance at low signal level, and therefore allow reducing the x-ray dose given to a patient.

The photon-counting detector that can be employed for the geometric calibration method of the present disclosure can be either of two types:
  (1) Indirect-Detection with Photon-Counting. Indirect detection has a scintillator layer that receives the x-ray signal and generates photons with energy levels corresponding to the x-ray spectral energy received; and
  (2) Direct-Detection with Photon-Counting. Direct detection has a sensitive semiconductor material that converts energy from x-ray photons to an electron flow. The energy level corresponds to the spectral energy of the received x-ray.

A further advantage of pulse counting relates to its capability to count pulses 180 at multiple threshold values, wherein each value is indicative of a spectral range of x-ray energy. Referring to the schematic diagram of FIG. 2B, two comparators 182a and 182b are shown for measuring pulse energy. In this particular configuration, a comparator 182a, a pulse shaper 184a, and a counter 186a provide a count 190a value for all pulses above a first threshold energy; similarly, a comparator 182b, a pulse shaper 184b, and a counter 186b account for only pulses above a higher, second threshold and provide a count 190b accordingly. Simple subtraction then identifies the different power levels achieved for each pulse. It can be appreciated that more than two threshold levels can be measured, using a corresponding arrangement of comparator circuitry, allowing pulse counts at any of a number of threshold values. In addition, thresholds can be selectable, such as adjustable to adjust the response of imaging sensor 170 to various photon energy levels. Thus, for example, an operator can use a set of preset thresholds for differentiating softer from denser tissue in the image that is finally generated.

In addition to setting minimum of floor thresholds (e.g., for noise reduction), embodiments of the present disclosure using multi-spectral x-ray imaging can also provide the option of using additional upper or maximum thresholds for photon energy. This upper threshold capability can be used for a number of functions, including reducing the generation of excessive noise signals such as from metal artifacts or x-rays passing directly through the direct detection material.

Figure 2B:
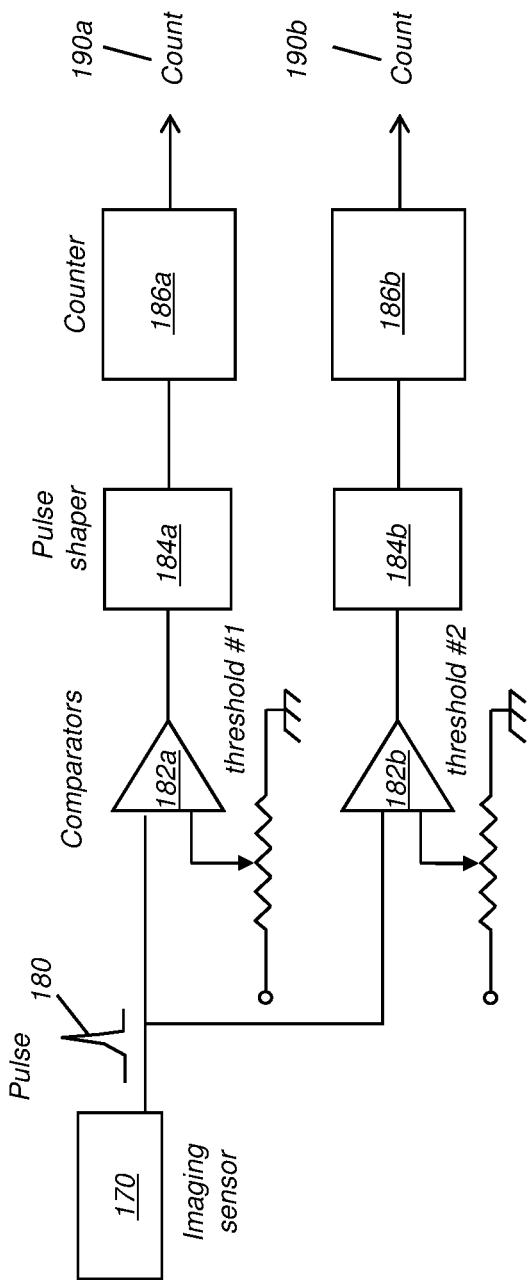
FIG. 2B is a schematic diagram that shows a photon-counting arrangement for measurement at two different energy levels.

The capability to count photons at different energy thresholds, as described with reference to FIG. 2B, allows the intraoral detector to differentiate between energy levels obtained from irradiating the subject at different x-ray wavelengths and provides added dimension to the image data that is provided as a result of each exposure. This capability, described as multi-spectral or "color" x-ray imaging, enables information to be obtained about the material composition of a subject pixel. As is well known, two materials A and B can have different coefficients of attenuation that vary with the level of radiation energy, exposure E. At a given exposure, material A attenuates a photon with an energy that corresponds to material A. Similarly, radiation impinging on material B attenuates a photon at a level that corresponds to material B. Where photons of these different energy values can be differentiated from each other, it is possible to identify one or both materials in the same pixel or voxel image element of the obtained image. This same basic behavior in response to radiation also allows some measure of capability to differentiate tissue types. Different linear absorption characteristics allow differentiation between various types of tissue, such as the capability for distinguishing between bone types.

Color x-ray using photon counting detectors provides for low cost and low dose color x-ray imaging. The use of multi-spectral or "color" x-ray imaging can have a number of potential benefits of value for intraoral imaging. These include minimization of metal artifacts, separate reconstruction of soft and hard tissue, more efficient segmentation algorithms for tooth and bone features, improved pathology detection for cancer and other disease, and detection of trace materials or contrast agents.

Among techniques that can be used for providing adjustable resolution and increasing acquisition speed are detector binning, described in more detail herein. Binning groups together uniform sets of adjacent sensor elements to provide a single, averaged value for the individual area of each set of pixels.

Source/Detector Alignment

Detector alignment can be difficult for dental or intraoral radiography. The detector position is within the patient's mouth and is not visible to the technician. Instead, the technician typically places the detector into some type of holder, and then inserts the holder into place in the mouth. The holder may have a bite plate or other type of supporting member that helps to position the detector appropriately. As is well known, holders of this type can be cumbersome and uncomfortable to the patient. Holders and other positioning devices are not error-proof, and positioning errors with these devices can mean that the images obtained are not suitable for diagnosis. Poorly aligned detectors can be the cause of problems such as cone cuts, missed apices, and elongation and related angulation or parallax errors, for example. These alignment problems can result in the need for re-takes, additional image captures to acquire an acceptable image. Re-takes are undesirable due to the additional x-ray radiation exposure to the patient and prolonged patient discomfort with the detector or sensor in the mouth.

Conventional x-ray sources have included aim indicators that help the technician adjust the position and angle of the x-ray source. Often these aim indicators use visible light to trace an outline that helps to center the radiation beam. These work well where the radiation detector can be seen, but fall short of what is needed where the detector is not visible, such as with intraoral imaging. The technician must guess or estimate both the position of the intraoral sensor and the angle of incidence of x-rays on the sensor.

Figures 3A, 3B:
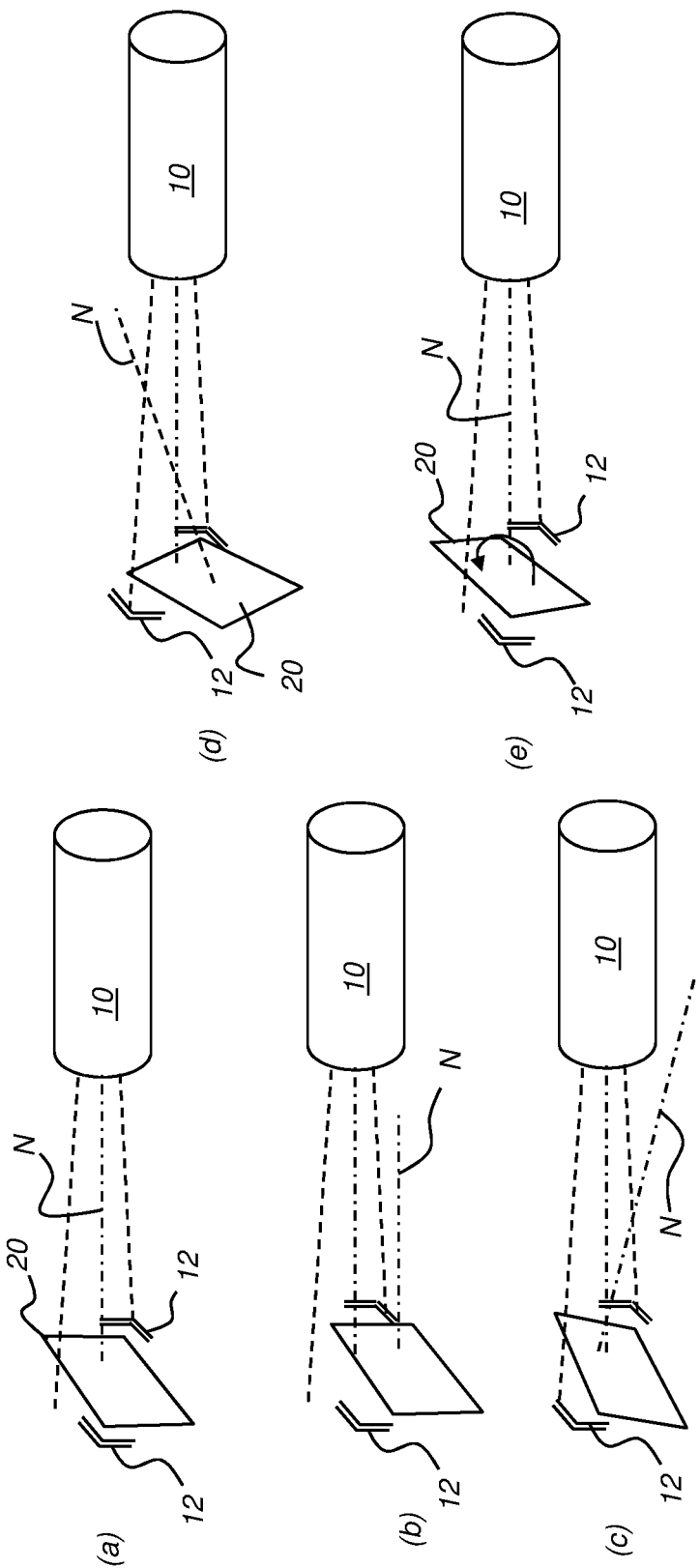
FIGS. 3A and 3B are simplified schematic block diagrams that show different aspects of the alignment problem.

The simplified schematic of FIGS. 3A and 3B show how mis-alignment between an x-ray source 10 and a detector 20 can occur. In these examples, x-ray source 10 provides visible light aim indices 12 used for aim centering. When correct aim alignment is achieved, shown at example (a), detector 20 is centered, as shown within aim indices 12. Aim is incorrect at examples (b) and (d).

For best imaging results, proper alignment with respect to angle, or angulation, is also needed. Incident radiation from x-ray source 10 is preferably orthogonal to detector 20 as shown in example (a). Line N in FIG. 3A, 3B indicates a normal, or orthogonal line, to the surface of detector 20. Examples (c) and (d) show incorrect angular alignment. In example (c), aim or centering is correct but angulation or pitch is incorrect. In example (d), both aim (centering) and angulation (pitch) are incorrect. In example (e), detector 20 is rotated in plane (roll).

It is instructive to note that the schematic examples of FIGS. 3A and 3B assume an orthogonal positioning of x-ray source 10 to detector 20. In some embodiments, an oblique orientation may be used.

Alignment and positioning are particularly important for volume imaging applications in which images taken at different angles are to be combined in some way to form volume image data.

In tomosynthesis, the relative movement between source and detector introduce further complexity into the alignment problem. It is generally most favorable for reconstruction processing to have the line or arc of movement disposed such that the spatial position of the source is within the same plane relative to the detector surface, or equidistant from the surface, so that movement aligns with pixel positions on the detector surface for each acquired projection image.

In order to better understand the parts and operation of the apparatus of the present disclosure, it is helpful to show how proper alignment can be detected by an imaging system. Referring to the schematic block diagram of FIG. 4, there is shown an intraoral imaging apparatus 22 that detects alignment of imaging detector 20 with x-ray source 10.

Figure 4:
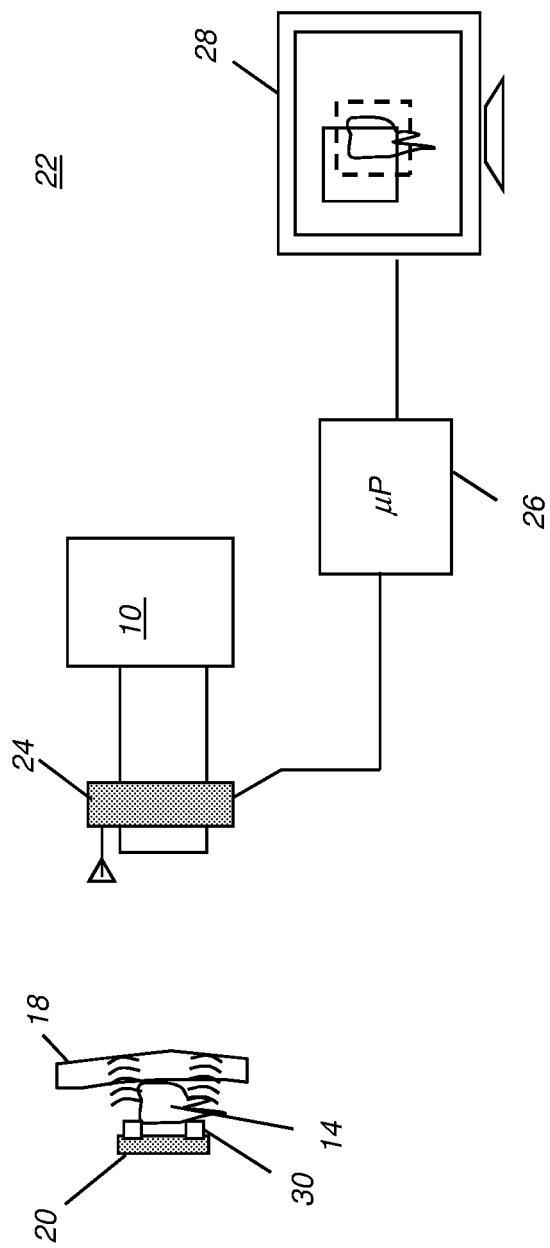
FIG. 4 is a schematic block diagram showing an imaging apparatus that calculates the lateral position and angular orientation of an intraoral image detector.

In the FIG. 4 arrangement, detector 20 is placed at a detector position that is adjacent to a tooth 14, inside a cheek 18 of the patient. Incorporated as part of detector 20 are a number of detectable elements 30, which are shown as electromagnetic signal emitters, such as radio-frequency (RF) emitters. Detectable elements 30 are typically spaced apart from each other in order to provide triangulation information. A sensor 24, itself aligned and positionally coupled with x-ray source 10, senses the presence of detectable element 30 in some way, such as by sensing emitted RF signals. Methods for energizing and sensing RF emitters, such as the tiny emitters used in RFID tags, for example, are well known to those in the signal detection arts. A control logic processor 26, in signal communication with one or more sensors 24, employs conventional trigonometric calculations based on the received signals from, or other detectable features of, detectable elements 30 and the known position of sensor 24 with relation to x-ray source 10. This is performed in order to determine the corresponding positional and angular alignment of detector 20 in the patient's mouth relative to x-ray source 10. An operator console display 28, a computer display monitor, then indicates alignment information for the operator and may recommend the needed adjustment settings. Sensors 24 are energizable to receive electromagnetic signals of one or more predetermined frequencies.

Figure 5:
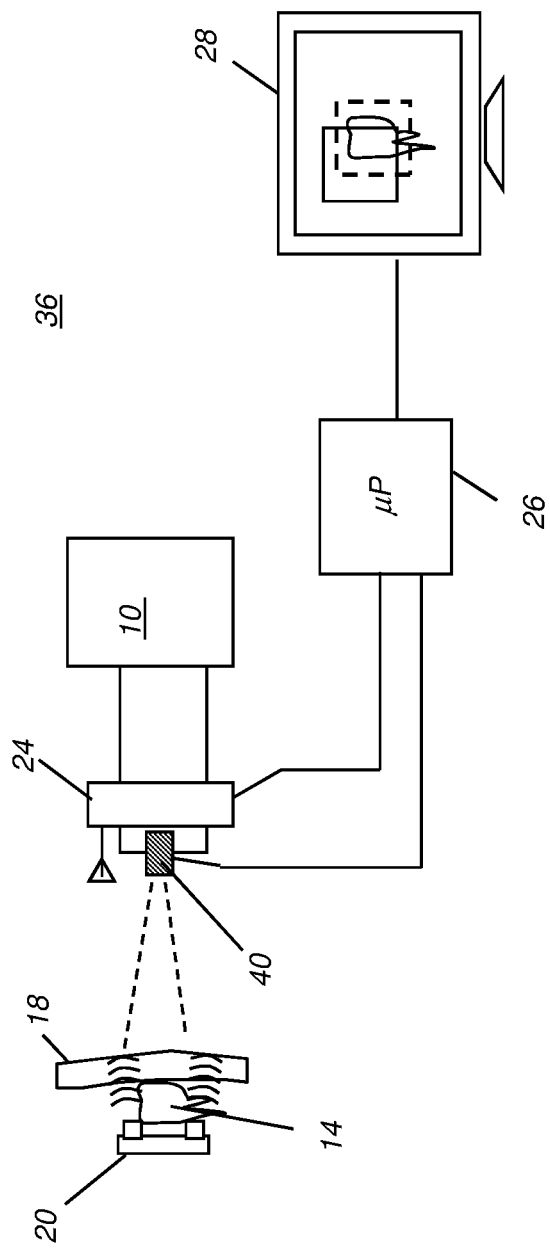
FIG. 5 is a schematic block diagram showing an imaging apparatus that calculates the lateral position and angular orientation of an intraoral image detector and projects a display onto the patient's cheek.

Certain example method and/or apparatus embodiments of the present disclosure improve upon the basic system of FIG. 4 by providing alignment information to the technician where it can be more easily used, particularly where this information is needed in order to obtain the individual images used for forming a volume image. Example alignment apparatuses of the present invention can project an image onto the cheek or other portion of the dental patient as a guide for proper alignment of the x-ray tube with respect to the position and angle of the detector. Referring to an embodiment of an imaging apparatus 36 in FIG. 5, control logic processor 26 obtains alignment information in similar manner to that described in FIG. 4. In addition, as shown in FIG. 5, control logic processor 26 can also be in image data signal communication with a projector 40 for projecting an image onto the patient's cheek 18, lips, or face.

Figure 6A:
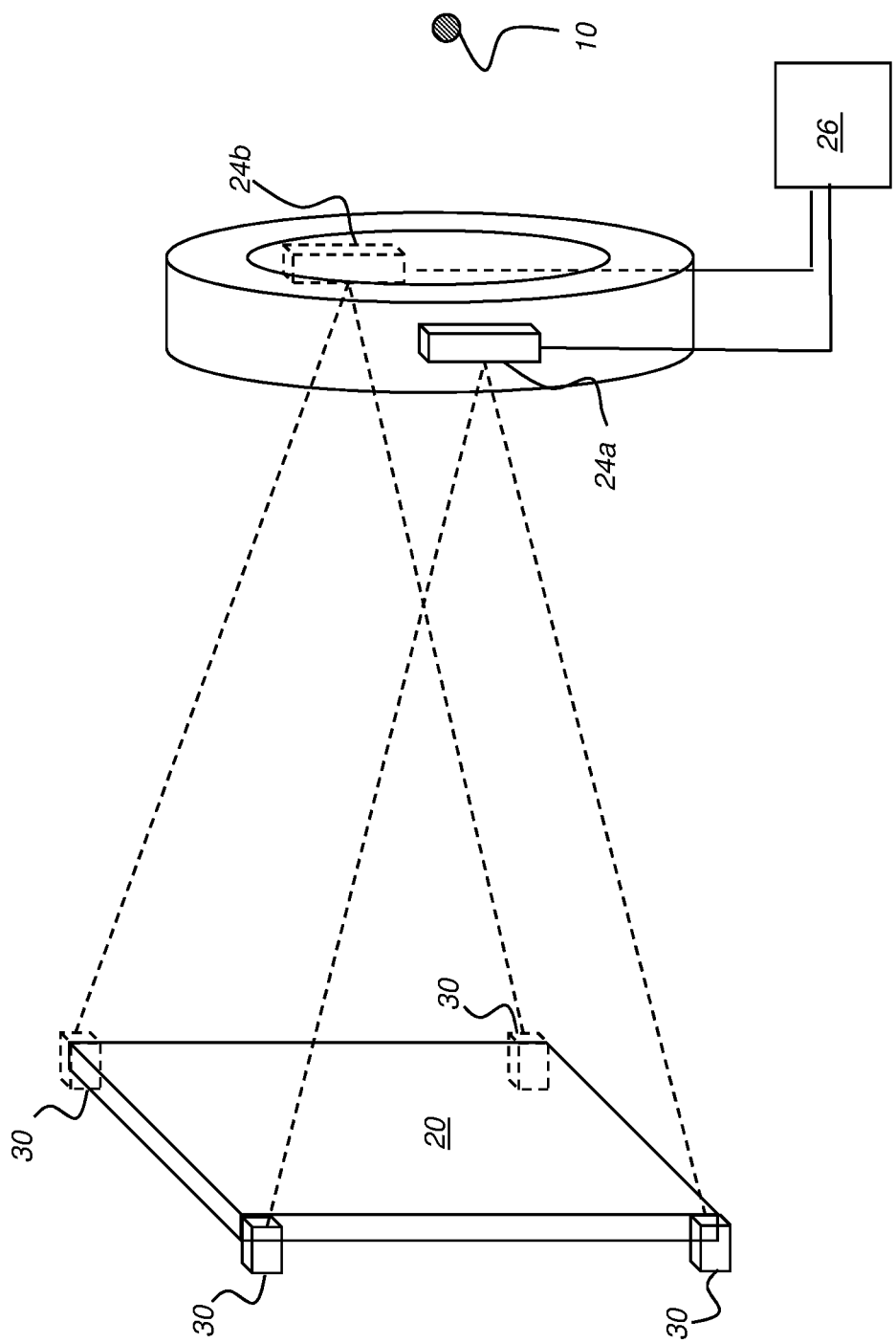
FIG. 6A is a schematic diagram that shows how triangulation is used for position detection in one example embodiment of the present invention.

The perspective view of FIG. 6A shows, in schematic form, how triangulation can be used to indicate position and angle of detector 20 in order to determine alignment offset in one embodiment. Sensors 24a and 24b, RF transceivers in one embodiment, are at a known position relative to the x-ray source 10, such as mounted near the x-ray source on the x-ray tube, for example. Signal emitters or other type of detectable elements 30 are typically disposed in pairs, positioned at corners of detector 20. Each detectable element 30 has a detectable feature that can be sensed by sensors 24a and 24b. In one embodiment, each detectable element 30 is an RF device that generates an electromagnetic field, such as in response to a transmitted signal from its corresponding signal receiver, sensors 24a or 24b. Phase, intensity, or other characteristic of the emitted electromagnetic field is measured at the corresponding sensors 24a and 24b, and is used in order to determine relative distance between emitting and receiving components. For the RF detection embodiment of FIG. 6A, for example, when signals for each pair of emitters, acting as detectable elements 30, are in phase, good alignment has been achieved. An out-of-phase condition indicates poor alignment and can indicate the needed direction for adjustment. Sensors 24a and 24b are in signal communication with control logic processor 26.

In a similar manner, relative signal strength could alternately be used to indicate the position and angle of detector 20 with respect to the x-ray source for determining alignment offset. Using this approach in an RF embodiment, the nearest signal emitter acting as detectable element 30 has, correspondingly, the strongest intensity signal at sensor 24$a$ or 24$b$. When the arrangement of FIG. 6A is used, signals of equal intensity emitted from all four emitters or other type of detectable element 30 indicate good alignment. When signal intensities vary, the pattern for their variation can be used to indicate which adjustments are needed. As one example, U.S. Patent Application Publication No. 2009/0060145, entitled "Positioning Adjustment of a Mobile Radiology Facility" by Tranchant et al., describes a position detection system that uses triangulation and sensing of multiple emitted signals to compute alignment positioning. It can be appreciated that any of a number of different configurations can be used for determining proper alignment using one or more sensors 24 and detectable elements 30, as is well known to those skilled in the signal processing and position sensing arts.

Figure 6B:
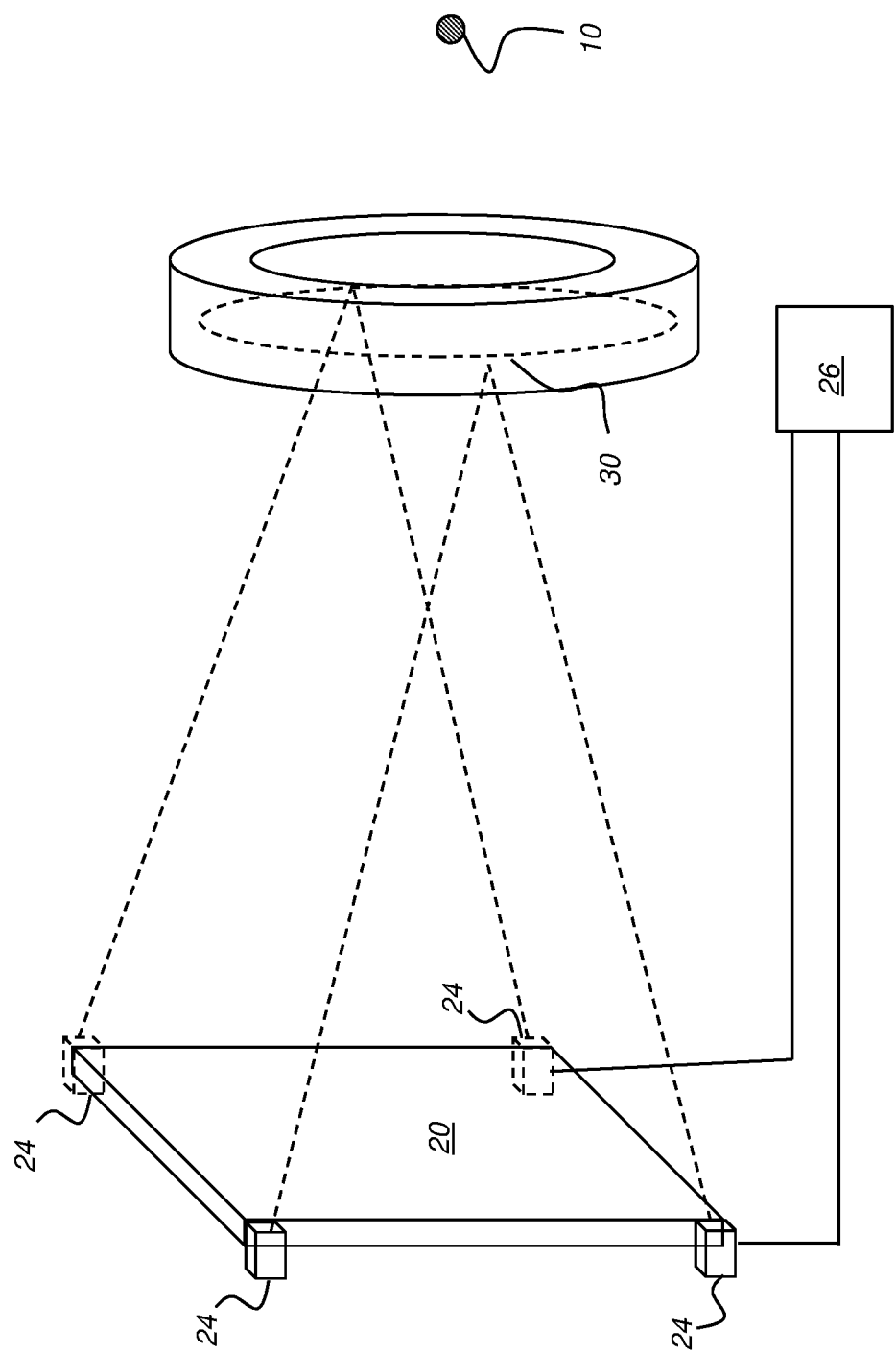
FIG. 6B is a schematic diagram that shows position detection in an alternate example embodiment of the present invention.

In one alternative embodiment, shown in FIG. 6B, the emitter-detector arrangement that was shown in FIG. 6A is reversed, so that one or more emitters that provide one or more detectable elements 30 are mechanically coupled to x-ray source 10 and two or more sensors 24 are attached to detector 20. In the embodiment shown in FIG. 6B, for example, detectable element 30, shown in dashed outline, is a coil that generates an electromagnetic field that is sensed by sensors 24. Sensors 24 are in signal communication with control logic processor 26, either through a direct (e.g., wired) or an indirect (e.g., wireless) connection.

Alternate Alignment Mechanisms

In one example embodiment, an intraoral scanner or other reflectance imaging sensor can be used as an aid to source alignment with the detector. The optical scan data obtained from a contour image or conventional reflectance image can be analyzed as a type of "scout" scan in order to determine the desired trajectory for the tomosynthesis scan.

In another example embodiment, ultrasound imaging can also be used as an alignment aid for source positioning. Ultrasound can be particularly useful with its capability to image soft tissue structures within the anatomy.

It should be noted that CNT source alignment can be adjustable to control the trajectory of relative positional change of the radiation source for each subsequent image.

Figure 6D:
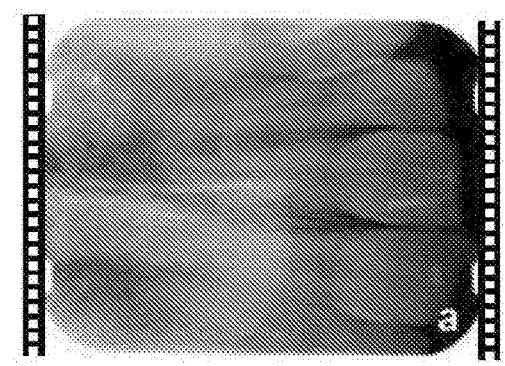
FIGS. 6D and 6E show how markers appear in the acquired image, along the borders of the imaged intraoral features.
Figure 6E:
Figure 6C:
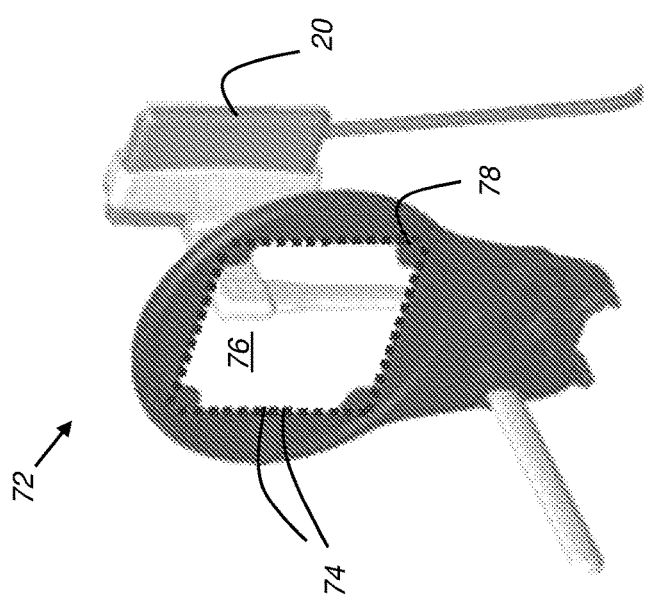
FIG. 6C shows a holder having an arrangement of radio-opaque alignment markers about a central opening.

One example method and/or apparatus embodiment according to the present application provides autofocus and alignment functions using an arrangement of embedded markers within a holder that is used for positioning the intraoral sensor. FIG. 6C shows a holder 72 for a frame 78 having an arrangement of radio-opaque markers 74 about a central opening 76 that orients the x-ray source 10 (not shown in FIG. 6C). FIGS. 6D and 6E show how the markers 74 appear in the acquired image, along the borders of the imaged intraoral features. Using the alignment markers allows image processing to correlate the positions of successively acquired images and to accurately register the projection images to each other for subsequent reconstruction.

It can be observed that solutions such as those shown in FIGS. 6A-6C can be used for alignment in any number of source-to-detector arrangements, as is described in more detail herein.

Projection of Outline Onto Patient or Other Alignment Feedback

Figure 7A:
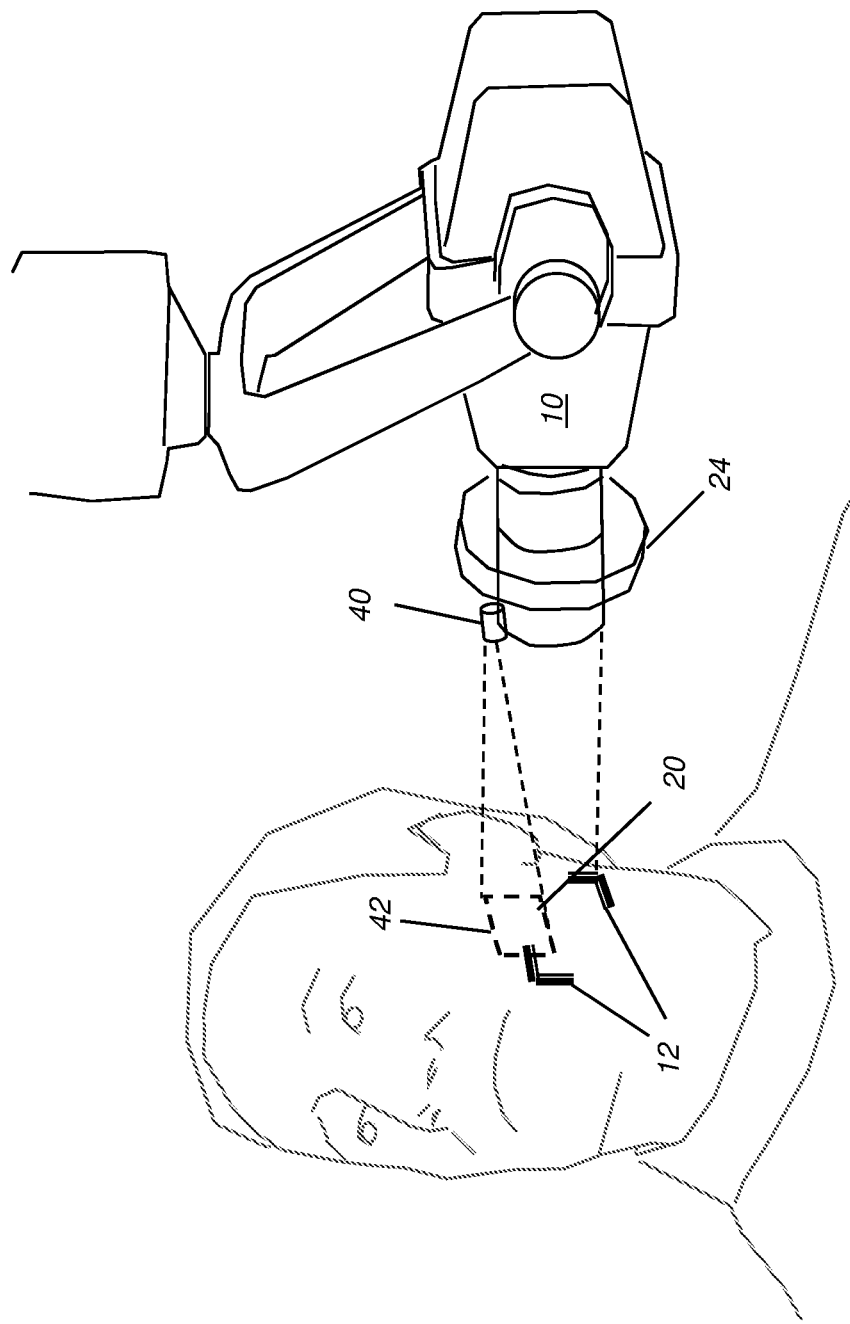
FIG. 7A is a perspective view showing an intraoral x-ray imaging apparatus according to one example embodiment, in which alignment is not correct.
Figure 7B:
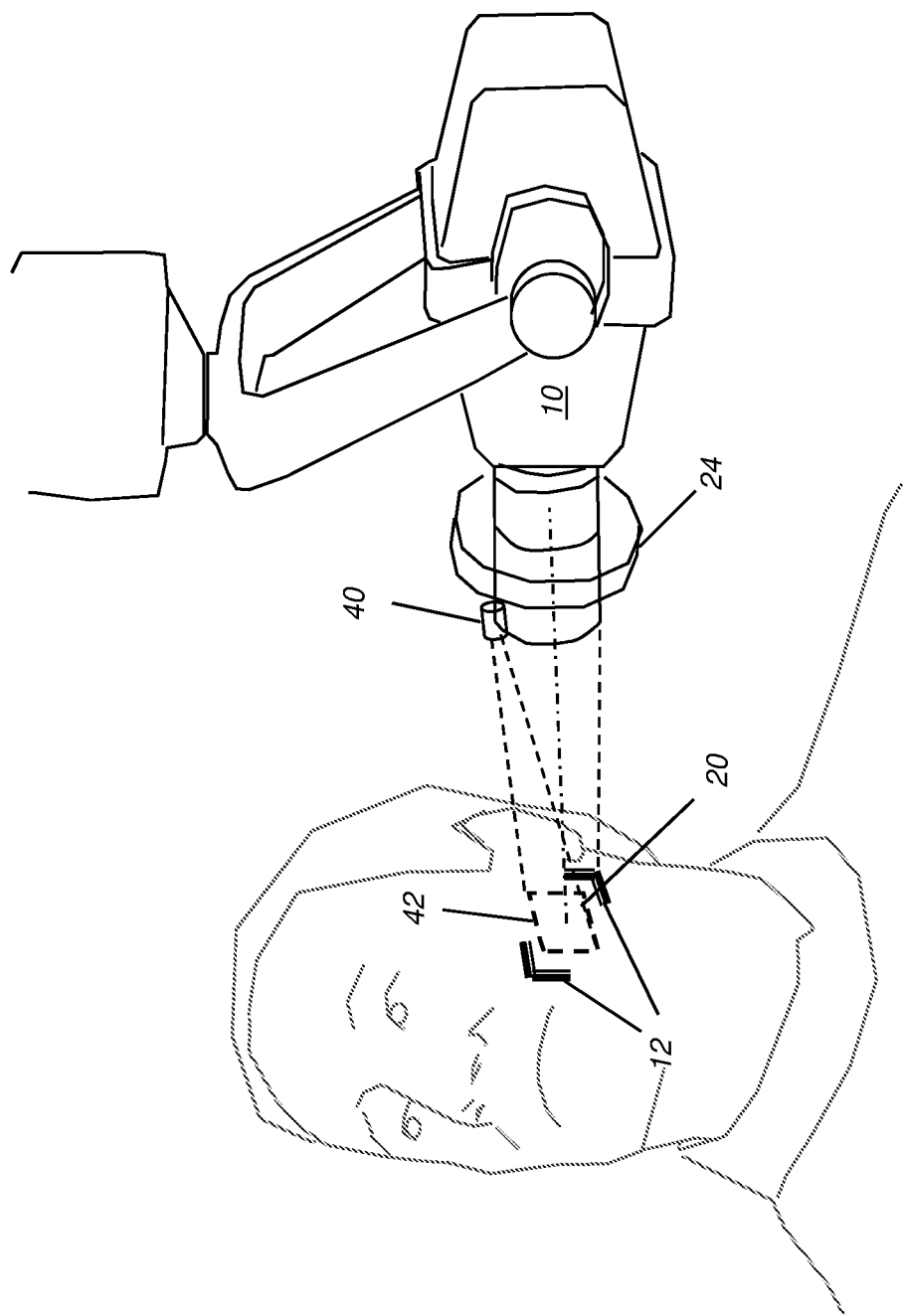
FIG. 7B is a perspective view showing an intraoral x-ray imaging apparatus according to one example embodiment, in which alignment is correct.

Referring to the perspective views of FIGS. 7A and 7B, the added advantage of example embodiments of the present invention that provide optional image projection is shown. Projector 40, positionally coupled to x-ray source 10, such as mounted in position toward the end of the x-ray tube or on some other portion of the x-ray system, for example, projects a two-dimensional image onto the patient's cheek in order to indicate a position 42 of the concealed detector 20 (shown in dotted outline) and, unless already provided by the x-ray source 10, also to indicate the aim indices 12 of the x-ray source. FIG. 7A shows an example in which aim alignment is incorrect, since position 42 is not aligned with aim indices 12. FIG. 7B shows an example in which aim alignment is correct, with position 42 centered between aim indices 12.

Projector 40 can be any of a number of types of imaging projector that can be mounted onto x-ray source 10. In one embodiment, projector 40 is a pico-projector, such as a Pico Projector Display from Microvision Inc., Redmond, WA, USA, for example. Devices such as these are advantaged for a number of reasons, including small size, low weight, and low power requirements. These pico-projectors, used in cell-phone and other highly portable electronic devices, scan one or more low-power lasers onto a display surface. The pico-projector requires a minimum of optical components for projection over a range of distances. The laser itself is turned on and off rapidly as needed, so that power is consumed only for those image pixels that are projected. This allows the pico-projector to operate at low power levels, so that battery power could be used for projector 40. Alternate embodiments use other types of electronic imaging projectors, such as those that employ a digital micromirror array such as the Digital Light Processor (DLP) from Texas Instruments, Inc.; an array of micro-electromechanical grating light valves, such as the Grating Light Valve (GLV) device from Silicon Light Machines, Inc.; or, a liquid crystal device (LCD) including a Liquid Crystal on Silicon (LCOS) device.

Where lasers are used as illumination sources in projector 40, additional measures can be taken to minimize incidence of coherent laser light to the eyes of the patient or practitioner. Very low power lasers can be used, such as solid-state lasers, at scanning rates that deliver only a very small amount of light intensity at any point. A diffusive element may be provided in the light path, for example, to provide some scattering of the laser light, reducing intensity with little or no effect on the quality or utility of the projected image. Light-emitting diodes (LEDs) or other low-power solid-state illumination sources could alternately be used, such as organic LED (OLED) devices.

The image that is projected by projector 40 (FIGS. 7A and 7B) can have image content that is any of a number of forms and may include both aim indicia 12 for the x-ray source and position 42 indicator for detector 20. Alternately, where aim indicia 12 are already provided by the x-ray system, projector 40 may only provide a projection showing position 42. Because projector 40 employs a two-dimensional imaging device, the displayed image can have multiple parts and may include additional text fields, direction markers, and other elements. Position 42 may be shown in outline form, as shown in FIGS. 7A and 7B, or may be represented in some other way. In one example embodiment, the value of angular offset of detector 20 is indicated on the patient's cheek as a displayed numerical message. Alternately, animation or other capabilities of projector 40 could be used to provide, as image content, additional position and angle information.

Color can be used to help indicate the relative amount of alignment offset in various ways. For example, even with the outline of detector 20 projected on the cheek surface, it can be difficult for the technician to know how to adjust for angular alignment. Display of indicia 12 and position 42 in different colors can help to guide the technician in adjusting the angle of the x-ray tube until both aim indicia 12 and position 42 display in the same color, for example. Blinking of the display or of different portions of the displayed elements can also help to indicate and guide alignment adjustments. An audible beep may be provided to indicate acceptable or unacceptable alignment. Stationary indicators, such as arrows or target symbols can be projected as image content onto the cheek of the patient. Animation can be provided to guide adjustment.

In one example embodiment, the projected image from projector 40 (FIG. 7B) instructs the technician on how to re-aim x-ray source 10 or how to adjust the position of the treatment chair in order to set up for the next image in the sequence. Projected color, patterning, alphanumeric text, animation, flashing or blinking, or other mechanism can be used to guide positioning adjustment between image captures.

A patient head support apparatus is provided in order to stabilize head position during the tomosynthesis image acquisition cycle. It should be noted that any type of headrest or other support mechanism cannot be metal or other highly radio-opaque material. The patient head support apparatus can be donut-shaped, expandable, or inflatable, for example.

Collimation

For select example method and/or apparatus embodiments, collimation is needed in order to constrain the radiation field to the region of interest (ROI) within the patient's mouth.

One beneficial aspect of collimation relates to eliminating or reducing cone-cutting, in which excess radiation from the projected x-ray is incident on areas outside the region of interest.

A difficulty with distributed source arrangements such as CNT arrays relates to the need for appropriate collimation of the radiation. Among its functions, collimation controls the spread of radiation energy so that radiation is appropriately directed to the anatomy of interest and that the radiation field does not extend beyond the outer edges of the imaging receiver. Collimation also helps to reduce scatter. With CNT and other types of small x-ray sources in an array, collimation presents particular challenges. One set of problems relate to dimensional constraints. Because the spacing between x-ray sources is typically small, it can be difficult to effectively isolate the radiation energy from any individual source; crosstalk can occur, making it difficult to clearly define edges of the radiation field. Still other complexity relates to identifying the radiation field for imaging from each source. With conventional radiography sources, the problem is readily solved: a light source that is coupled to the radiography source can be used to outline or otherwise highlight the radiation field, using the collimator edges themselves to outline the extent of the radiation field. However, it can be impractical or impossible to provide the corresponding dual-use arrangement using collimator openings provided for CNT and other types of distributed array sources.

The simplified schematic view of FIG. 8A shows some of the geometric considerations and relationships that relate to x-ray collimation for a single x-ray source 210 in general and establish some definitions useful in subsequent description of collimation for an array of x-ray sources. X-ray source 210 is idealized as a point source, to a first approximation. Radiant energy from source 210 is directed along a radiation path that extends through a first aperture 122 that is typically very close to source 210 and may even be optional under some conditions for very small x-ray sources. The radiant energy then continues along the radiation path through a second aperture 124 that shapes an x-ray field 130 on a detector 20. The shape and dimensions of the radiation path that determine the aspect ratio of x-ray field 130 are then determined by the geometric constraints such as aperture 122, 124 size and location relative to the source 210 and to each other and source-to-image distance (SID). The shape of x-ray field 130 is typically bounded by the dimensions of detector 20 but may be smaller and of a different shape, depending on the anatomy being imaged. It must be noted that FIG. 8A shows geometric relationships for a single source 210; embodiments described subsequently have multiple x-ray sources 210, each having collimation along its radiation path in a similar manner to that shown in FIG. 8A.

According to an example embodiment according to the application shown in FIG. 8B, array of sources 20 can be used with a rotatable collimator plate assembly 220 to form radiation fields of various shapes and aspect ratios depending on the dimensions of apertures 222a, 222b, rotation angle of collimator plate assembly 220, and the arrangement of corresponding sources 20 that are energized in the energization sequence. Thus, for example, with respect to FIG. 8B, a radiation source assembly 200 has a generally square shape with sources 20 distributed along the sides of the square. Collimator plate assembly 220 in FIG. 8B has apertures 222a and 222b of more than one aspect ratio. One set of apertures 222a is square; the other apertures 222b are rectangular. By rotating collimator plate assembly 220 to different positions and energizing the corresponding apertured sources 20 for the given radiation field shape, the sources 20 can be used in sequence to provide the needed radiation field shape and angular change for tomosynthesis.

Figure 8E:
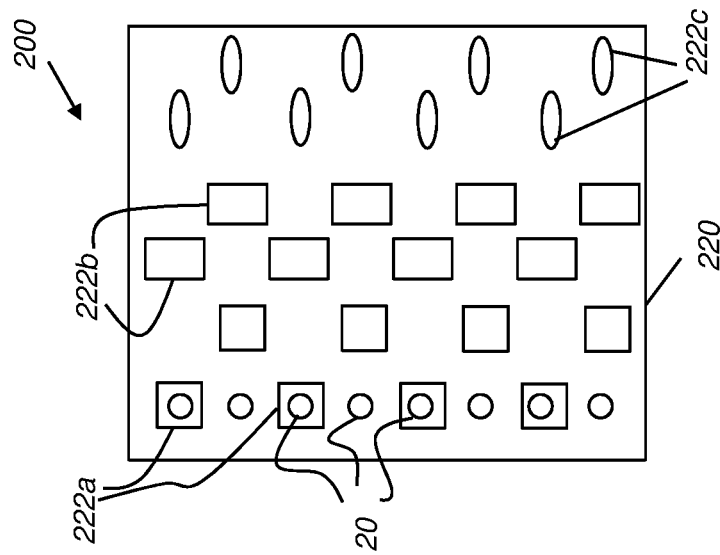
FIG. 8E is a bottom view that shows a collimator plate having paired sets of apertures of different aspect ratios.
Figure 8D:
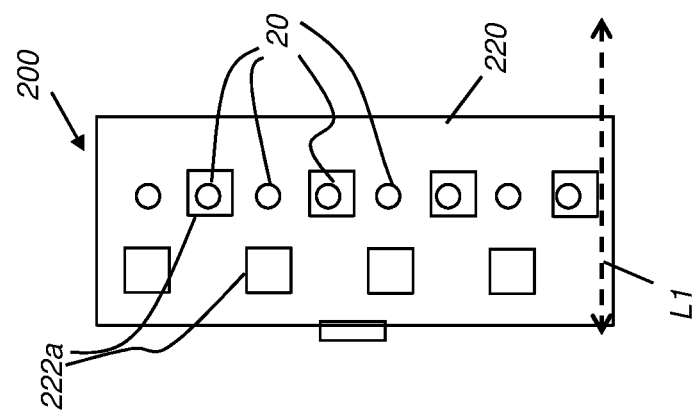
FIGS. 8C and 8D are bottom views that show an alternate collimator plate arrangement that is translated in a linear direction to position different sets of apertures over different subsets of the radiation source array.
Figure 8C:
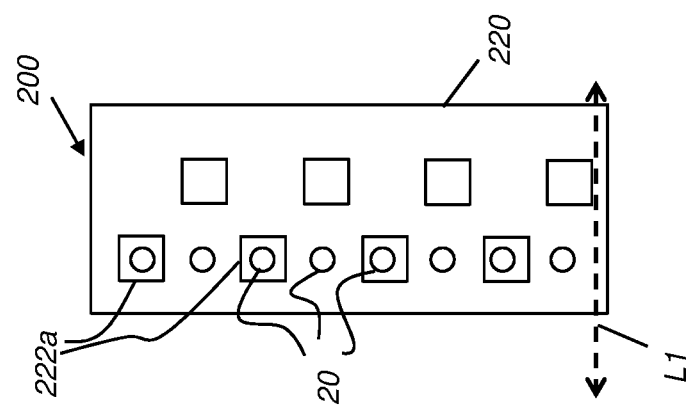

FIGS. 8C and 8D show another alternate arrangement in which collimator plate assembly 220 is translatable back and forth in a single direction, along the direction indicated by a line L1. In this example, radiation source assembly 200 is a linear array of sources 20. A set of square apertures 222a are arranged so that a subset of half of the apertures align to sources 20 with plate assembly 220 in a first position (FIG. 8C) and the subset with the other half of the apertures align to sources 20 with plate assembly 220 in a second position (FIG. 8D). FIG. 8E shows another arrangement, in which three different types of apertures are provided, a set of square apertures 222a in two subsets to be positioned in similar fashion to those shown in FIGS. 8C and 8D, a set of rectangular apertures 222b, and a set of oval apertures 222c, also used in a similar manner. Aperture 222 shapes can be inter-mixed (not shown).

Figure 8G:
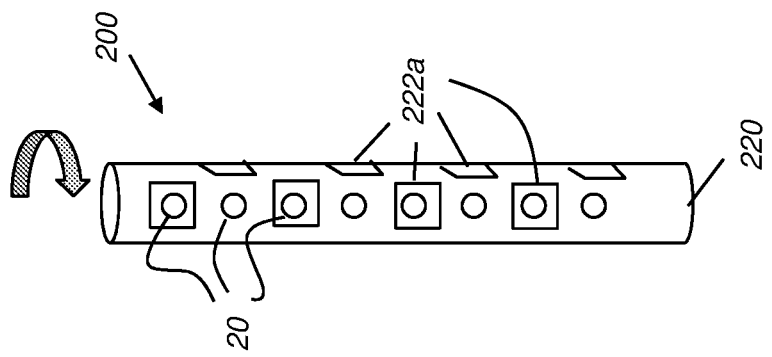
FIG. 8G is a view of a collimator that is curved and translated by rotating about a linear distributed source array.
Figure 8F:
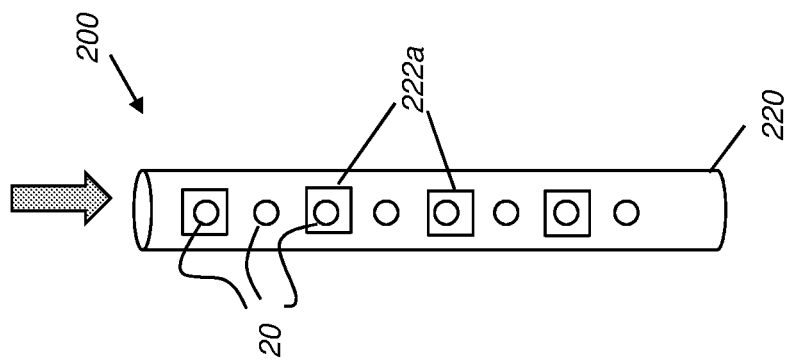
FIG. 8F is a view of a collimator that is curved and translated linearly along a linear distributed source array.

FIGS. 8F and 8G show another alternate embodiment in which collimator plate assembly 220 has a generally curved or tubular shape, with apertures 222a arranged for x-ray sources 20 in a linear radiation source assembly 200. In the arrangement of FIG. 8F, collimator plate assembly 220 is moved in linear fashion to shift apertures 222a between subsets of x-ray sources 20. In the arrangement of FIG. 8G, collimator plate assembly 220 is rotated about the linear array to shift apertures 222a between subsets of x-ray sources 20.

Collimator plate assembly 220 can be formed from a pair of metal plates, spaced apart from each other to form apertures 122 and 124 (FIG. 8A) and with apertures 124 sized and positioned for suitable beam shaping. Apertures are aligned with source 20 positions based on the needed beam profile and angle. For collimation control, near-source apertures 122 can be in fixed positions, with only the far apertures 124 adjustable.

Scan Sequence for Tomosynthesis Imaging

The alignment apparatus that is provided by the triangulation sensing apparatus of FIG. 6A or 6B can be used to assist in capturing a series of images of the same tooth or other structure, taken in quick succession and each with a slightly different positional relationship of the x-ray source to the detector, for forming a limited-depth volume image. As noted in the background section given previously, this type of volume imaging can have diagnostic value and advantages over a single x-ray image, but without requiring the expense and dose requirements of full-fledged CBCT imaging. In addition, unlike with CBCT imaging, the limited-depth volume image from tomosynthesis can be acquired with the patient seated in the treatment chair.

Figure 9A:
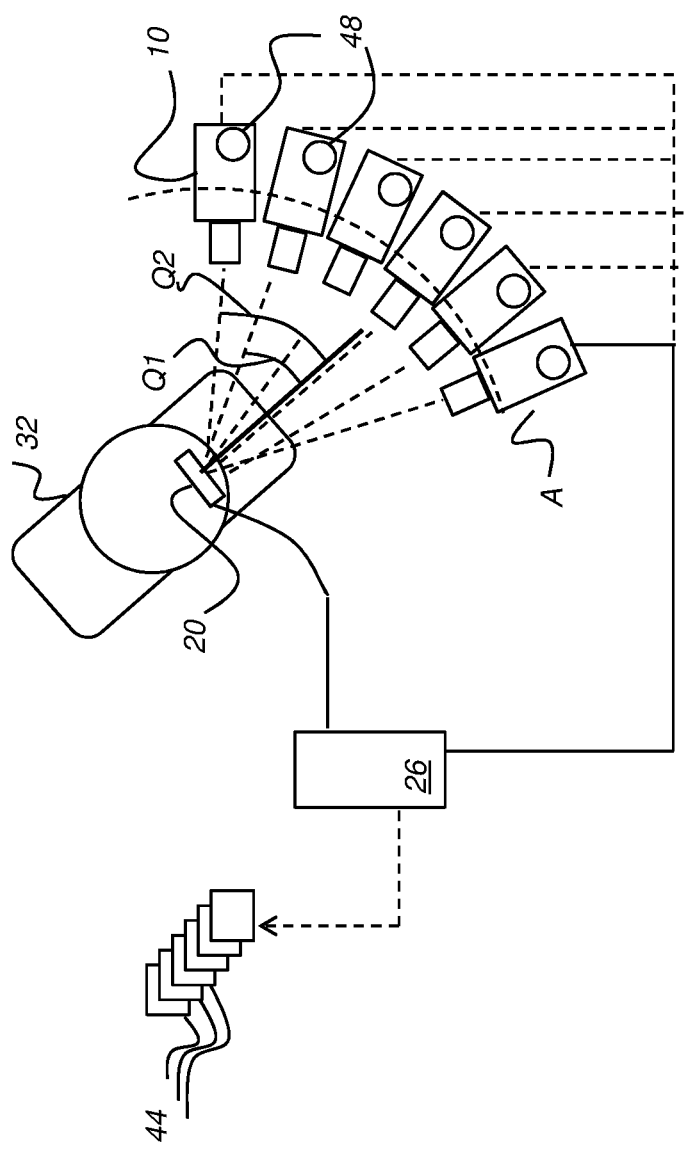
FIG. 9A is a schematic block diagram that shows an imaging pattern used for obtaining a volume image from a limited number of x-rays.

Referring to FIG. 9A, there is shown, from a top view, a schematic block diagram of an imaging pattern used for obtaining a limited-depth volume image from a patient 32 using a limited number of x-rays from a single source 10 and a digital detector. X-ray source 10 is used to direct exposure to detector 20 from a number of angular orientations, shown as capture or exposure angles in FIG. 9A, along a non-linear, curved or arcuate path A. At each of two or more positional relationships of the x-ray source to the detector, with two called out by way of example at angles Q1 and Q2 in FIG. 9A, radiation energy is directed to detector 20 and the corresponding image data from the digital detector obtained by control logic processor 26 and stored as a component or projection image 44, indexed according to the relative acquisition geometry for the image, such as by the exposure angle orientation. In this way, one component image 44 is obtained and stored for each paired positional relationship of the x-ray source to the detector, alternately considered as each exposure angle. Control logic processor 26 can then generate a 3D volume image as a composite image, using the combined data from the individual component 2D projection images 44.

It should be noted that the pattern traced by changes in the relative position of the x-ray emitter to the detector, as shown in the top view of FIG. 9A for example, can be linear or curved.

Additional sensing components and logic associated therewith are used to provide source-detector positional and angular information about each image that is obtained. In one embodiment, for example, fixed positional and angular coordinates are assigned to an initial spatial position and relative angular orientation of x-ray source 10. Then, system logic records the changed relative position and angle that correspond to each imaging position in the series of 2D projection images that are obtained. This data then provides the needed reference geometry for reconstruction of the 3D volume image from a series of 2D image captures. Spatial position data can be obtained in a number of ways, such as using an angular sensor 48 that is coupled with a gantry or other transport apparatus that is used for movement of x-ray source 10, for example.

Figure 9B:
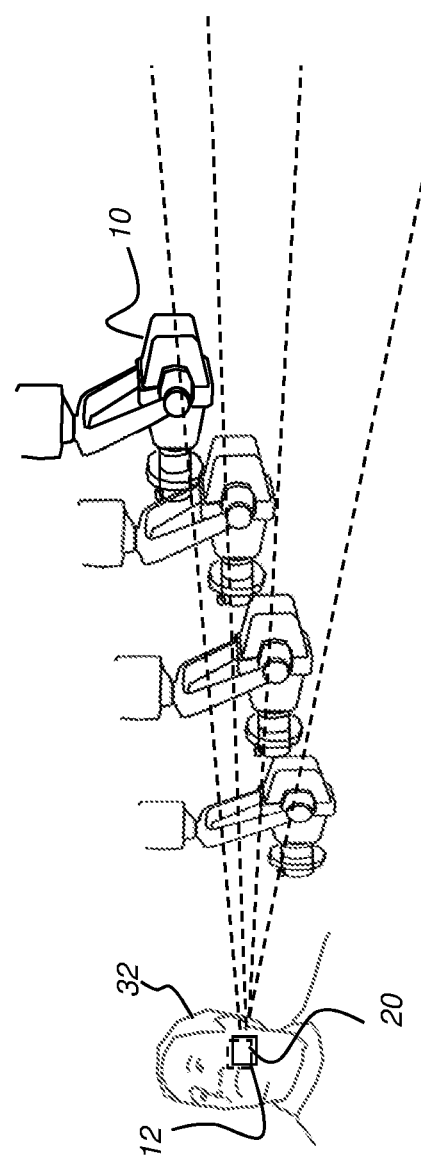
FIG. 9B is a perspective view showing how different positions of the x-ray emitter relative to the patient provide individual images for use in forming a volume image.

In order for the limited-angle volume imaging of tomosynthesis to work correctly, the angular orientation and spatial disposition of x-ray source 10 relative to detector 20 must be known for each projection image acquired throughout the imaging cycle, so that the component data that is obtained can be properly aligned and correlated between projection images. For the embodiment shown in FIG. 9A and in the perspective view of FIG. 9B, the head of patient 32 and spatial position of detector 20 (shown in dashed outline in FIG. 9B) are rigidly fixed in position while x-ray source 10 is moved orbitally from one relative angular orientation to the next. It may be necessary to mechanically fix the spatial position of detector 20 relative to the subject that is being imaged. With respect to FIGS. 9A and 9B, for example, one or more bite blocks or a clip-on device may be useful for rigidly fixing detector 20 at a position within the mouth of patient 32.

Figure 10A:
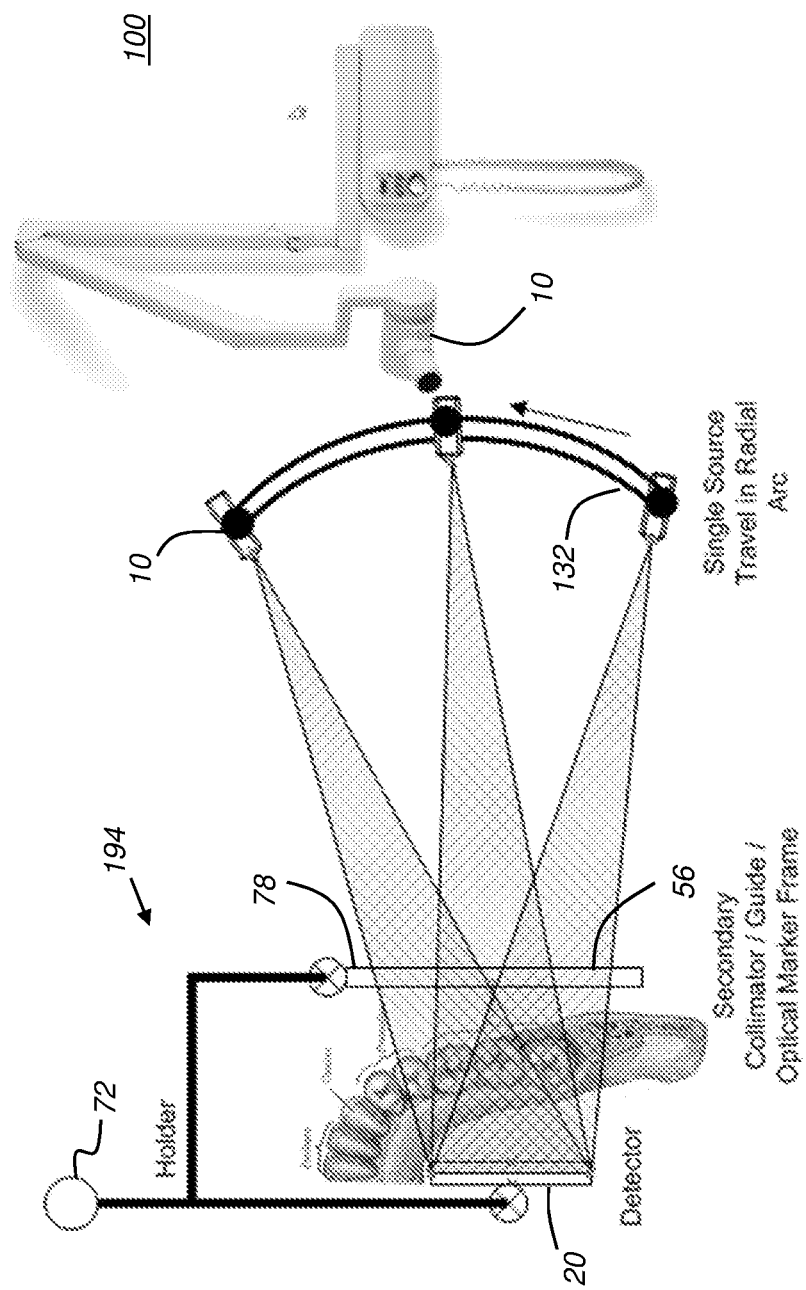
FIG. 10A is a schematic diagram that shows an intraoral imaging apparatus for tomosynthesis imaging with the x-ray source transported along an arcuate track.
Figure 10B:
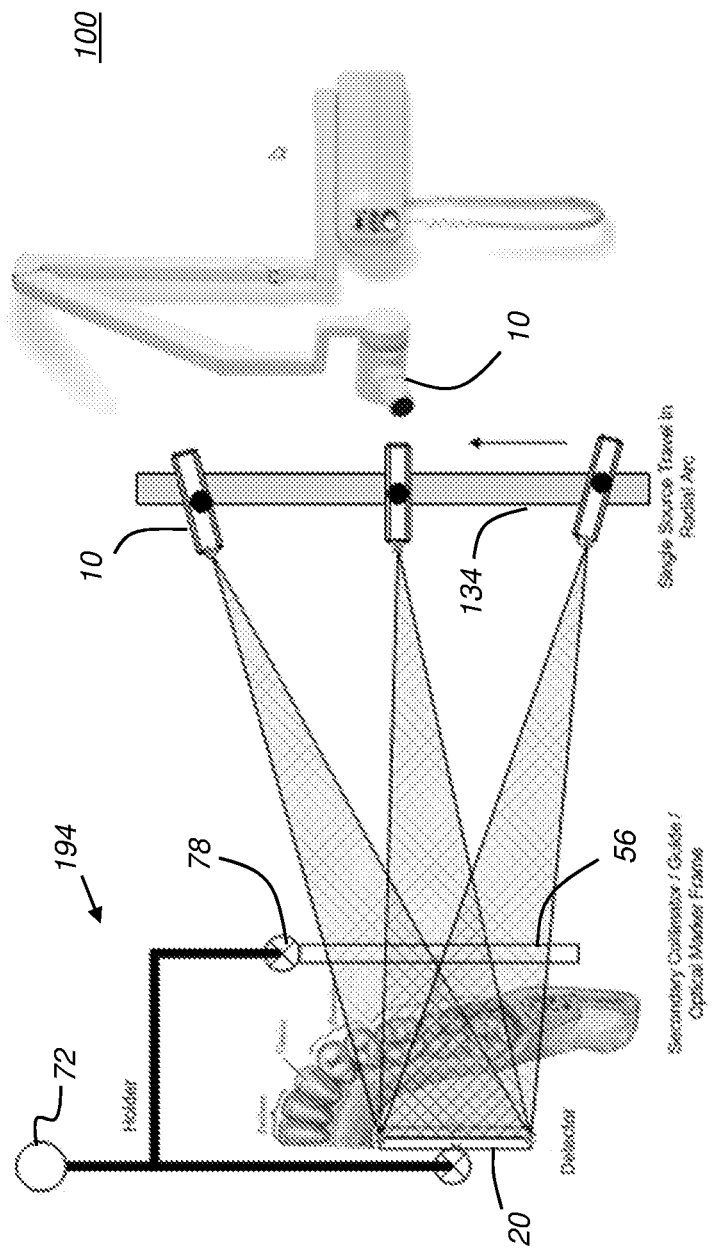
FIG. 10B is a schematic diagram that shows an intraoral imaging apparatus for tomosynthesis imaging with the x-ray source transported along a linear track.

FIG. 10A is a schematic diagram that shows an example intraoral imaging apparatus for tomosynthesis imaging with x-ray source 10 transported along a curved or arcuate track 132. Arcuate track 132 is curved to approximate an arc that is substantially centered at the detector position. Detector 20 is held in the patient's mouth, mounted in holder 72. Holder 72 provides a type of positioning apparatus that correlates the detector position with respect to the collimator. Frame 78, suspended outside the mouth, provides an aim and alignment device for x-ray source 10 as well as a holder for positioning the secondary collimator 56. The schematic diagram of FIG. 10B shows a similar example arrangement for apparatus 100 using a linear track 134. In the FIG. 10B embodiment, the x-ray source 10 pivots to different angles as it is translated along the linear path, thereby emulating the radial arc translation of FIG. 10A.

In the FIGS. 10A and 10B embodiments, detector 20 is rigidly coupled to frame 78, as was shown previously in the example of FIG. 6C. Holder 72, acting as a positioning apparatus 194 for correlating detector and collimator positioning, fixes the relative position of detector 20 and frame 78. For different patient head sizes, different size holders or different holder settings can be used. Alternate example embodiments can use various arrangements of sensors and encoders to provide mechanical or sensed positioning apparatus for positioning of detector 20 relative to the collimator 56 and to frame 78, using signals obtained from one or more sensor and encoder devices.

The schematic top view of FIG. 10C shows an example frame 278 embodiment having multiple articulated sections 280a, 280b, 280c with an encoder 282 at each adjustable joint for reporting sensed extension and rotation data. This arrangement provides a positioning apparatus 194 that allows resizing for the patient and provides repositioning of detector 20 relative to collimator 56, with sensed data available for correlating component positions relative to a reference position and relative to each other. Alternately, an accelerometer or electromagnetic, magnetic, or radio-frequency (RF) sensing may be provided and used as positioning apparatus 194 for correlating detector 20 position to the secondary collimator 56 and relating these positions to the position of the x-ray source at any acquisition angle in a tomosynthesis sequence.

Figure 11B:
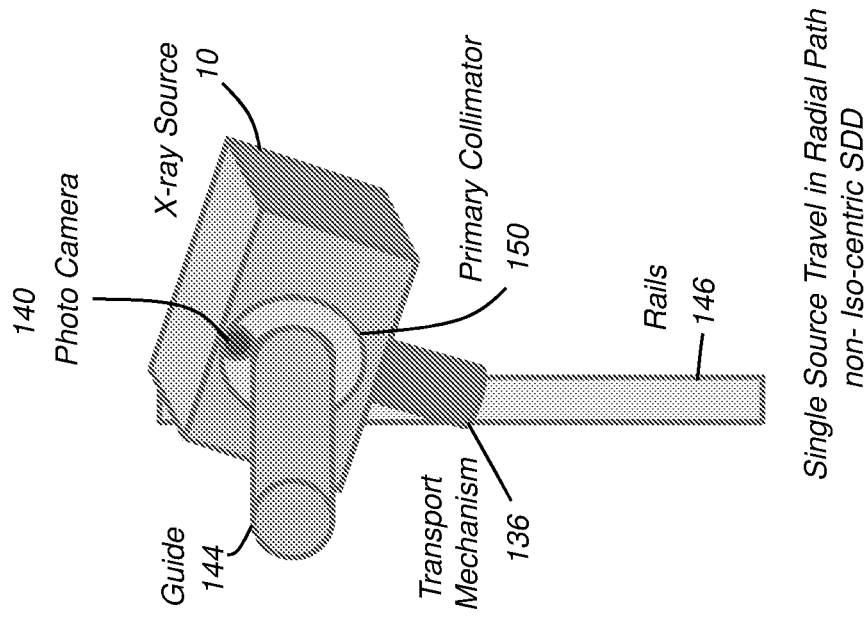
FIG. 11B is a perspective view that shows x-ray source configuration for the linear path arrangement shown in FIG. 10B.
Figure 11A:
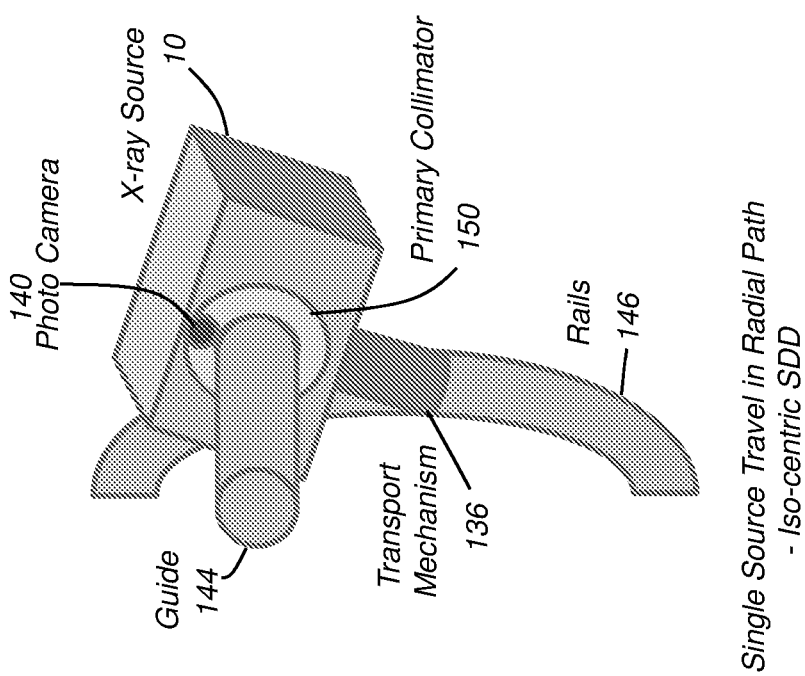
FIG. 11A is a perspective view that shows x-ray source configuration for the radial path arrangement shown in FIG. 10A.

FIG. 11A is a perspective view that shows a configuration of x-ray source 10 for the radial path arrangement shown in FIG. 10A that provides an example iso-centric signal-to-detector distance (SDD). X-ray source 10 travels along rails 146 to follow curved or arcuate track 132 (FIG. 10A), driven by a transport 136. Source 10 has a primary collimator 150 that is integral to the source hardware. In the context of the present disclosure, the designation "primary collimator" applies to any collimator(s) integral to, and not separable from, the x-ray source. A secondary collimator is provided using frame 78, as described subsequently. A camera 140 that is coupled to guide 144 can be used to assist in source/detector alignment. The perspective view of FIG.

11B shows an alternate configuration for an example linear transport, with a non-isocentric SDD.

Figure 12A:
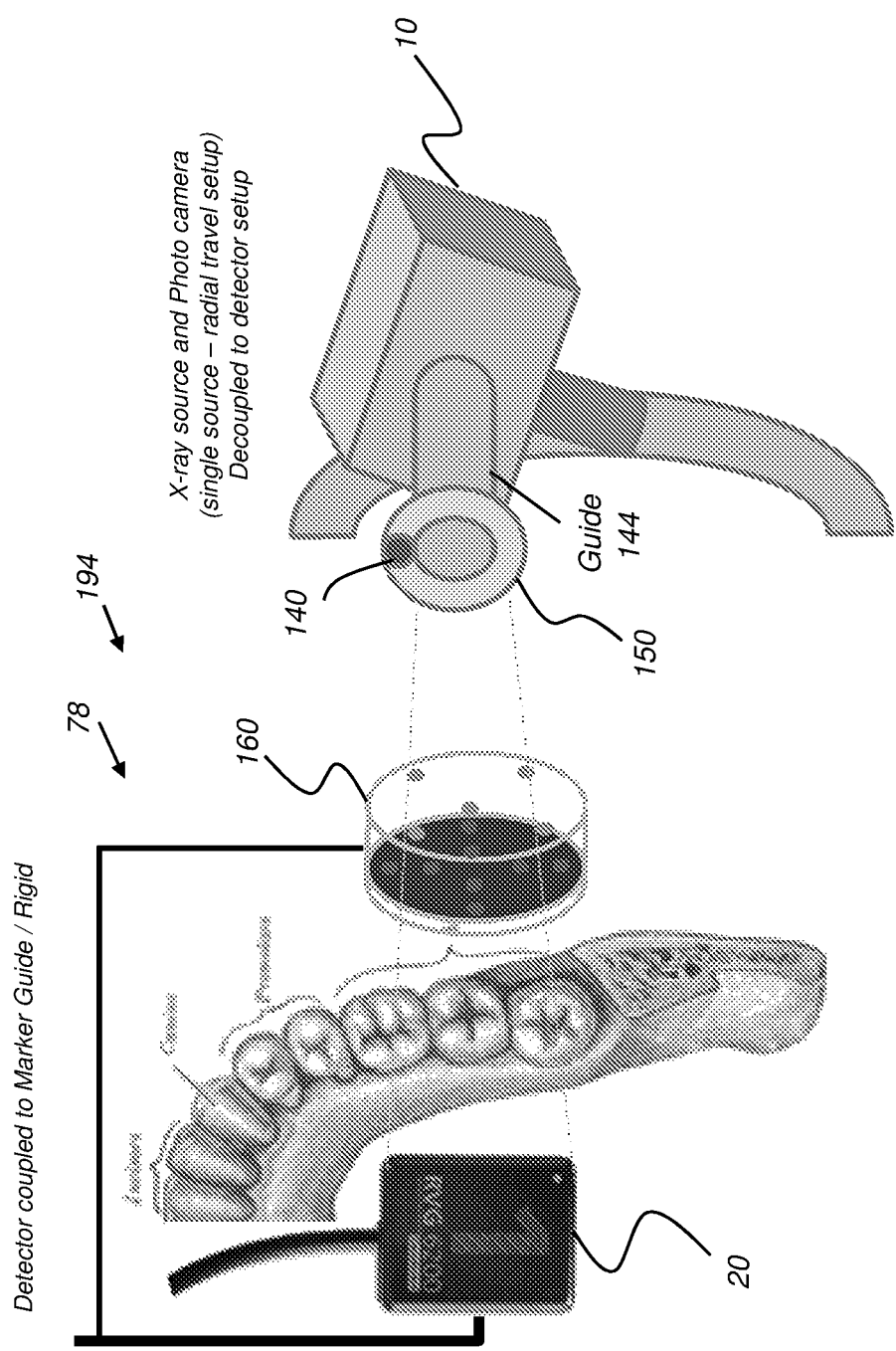
FIG. 12A is a schematic diagram that shows the use of a marker guide that is coupled with the intraoral detector.
Figure 12B:
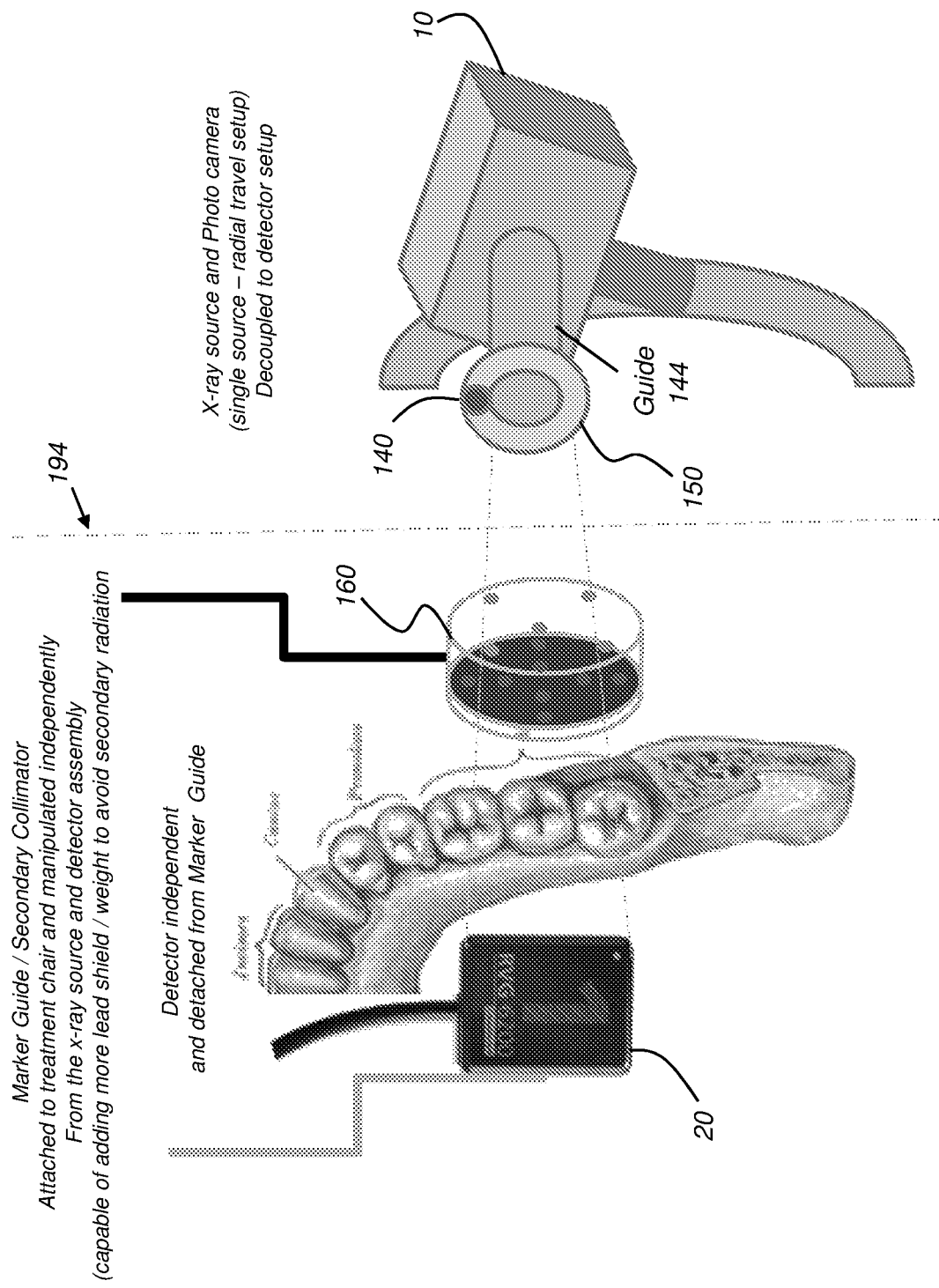
FIG. 12B is a schematic diagram that shows the use of a marker guide that is not directly coupled with the intraoral detector.

The schematic diagram of FIG. 12A shows the use of example marker guide embodiments 160 for markers coupled with intraoral detector 20 through frame 78. Marker guide 160, described in more detail herein, provides a number of functions that assist in alignment and collimation for the x-ray source 10 and relate the spatial position of the intraoral x-ray detector to the position of x-ray source 10. FIG. 12B shows a configuration with marker guide 160 un-coupled from detector 20.

When using radio-opaque markers, the spatial location of the source relative to the detector can be determined from image content, preferably around the edge of the FOV. The collimator and detector can be mechanically uncoupled with these markers provided in the radiation field and appearing in image content. When using radio-transparent optical markers, the collimator and sensor must be mechanically coupled or have some type of sensed positioning. Alternatively, optical markers can have an 3D orientation that allows the location of the source relative to the detector can be determined from camera, reflectance or optical image content, which can be sequentially or simultaneously obtained relative to the x-ray image content.

Figures 13A, 13B:
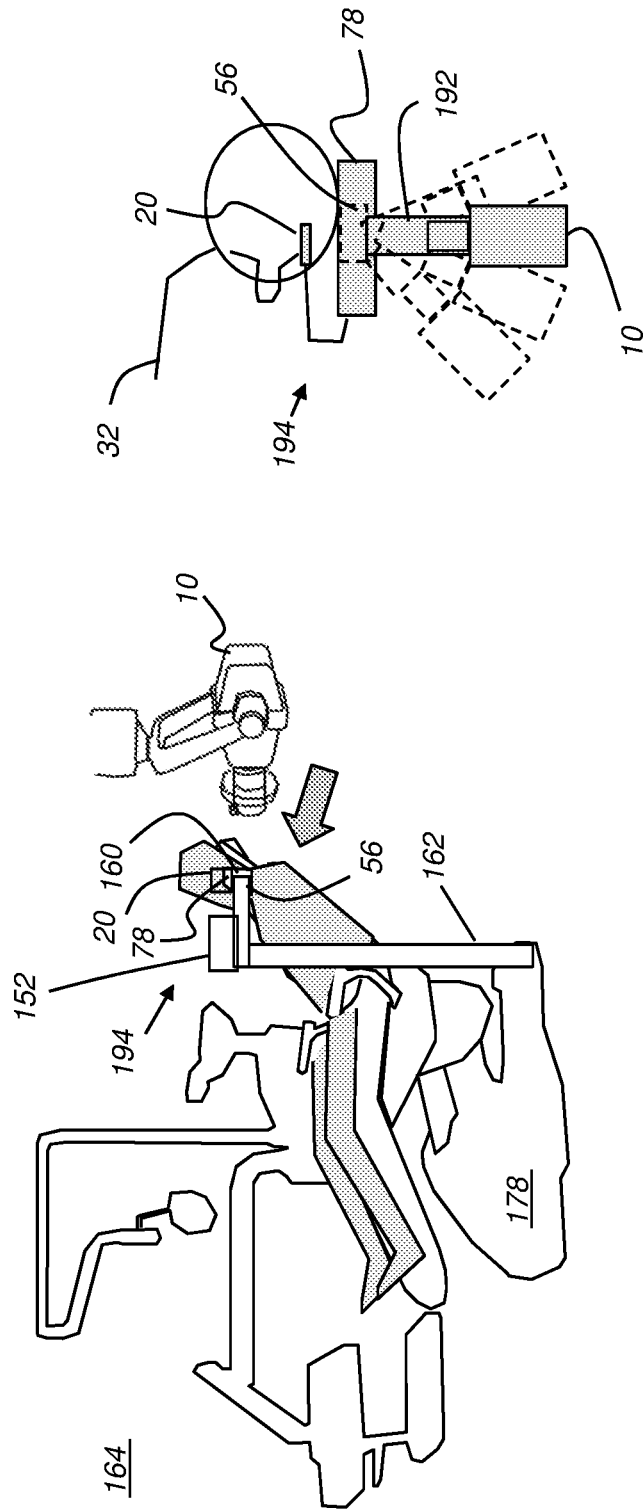
FIG. 13A shows a treatment system with chair and other apparatus for dental procedures.
FIG. 13B is a top view schematic that shows an arrangement with the x-ray source coupled to the collimator, chair, floor, or other equipment.

FIG. 13A shows an example treatment system 164 embodiment with chair and other apparatus for dental procedures. Frame 78 that houses marker guide 160 and provides a secondary collimator 56 supported from a mount 162 on system 164 such as from a base 198 or from the dental chair. Alternately, collimator 56 or its supporting frame can be mounted by a support extending from the ceiling. This arrangement, with mounting to stabilize collimator 56 position without requiring the device to be held by the patient, helps not only to support the weight of frame 78 that provides the secondary collimator, but can also help to provide inherent alignment as well as sensed alignment of x-ray source 10 to the patient and intraoral detector 20. As indicated by the arrow, x-ray source 10 can be moved toward frame 78, so that it is at the proper distance and alignment for the image acquisition sequence. Frame 78 can be part of a headrest, such as an adjustable headrest, for patient positioning to allow tomosynthesis imaging.

FIG. 13B is a top view schematic diagram that shows positioning of frame 78 with secondary collimator, wherein frame 78 is mounted to an example support embodiment that extends from the dental chair, from the ground or ceiling, or from another nearby support structure external to the patient. An arm 192 or other linkage or coupling device can also be mounted to frame 78 in order to guide positioning and movement of source 10 during tomosynthesis imaging. With this arrangement, source 10 is effectively coupled to the secondary collimator 56 of frame 78. This obviates the need for any type of alignment mechanism for alignment of source 10 to the secondary collimator. This arrangement can be used with radio-opaque or visible markers for indicating the relative position of the detector.

One or more sensors 152, such as an accelerometer or electromagnetic device such as a Hall sensor can be provided to detect movement and positioning of frame 78 on mount 162, helping to determine accurate registration of marker guide 160 relative to detector 20 and to x-ray source 10.

Marker Guide Composition

Figure 14A:
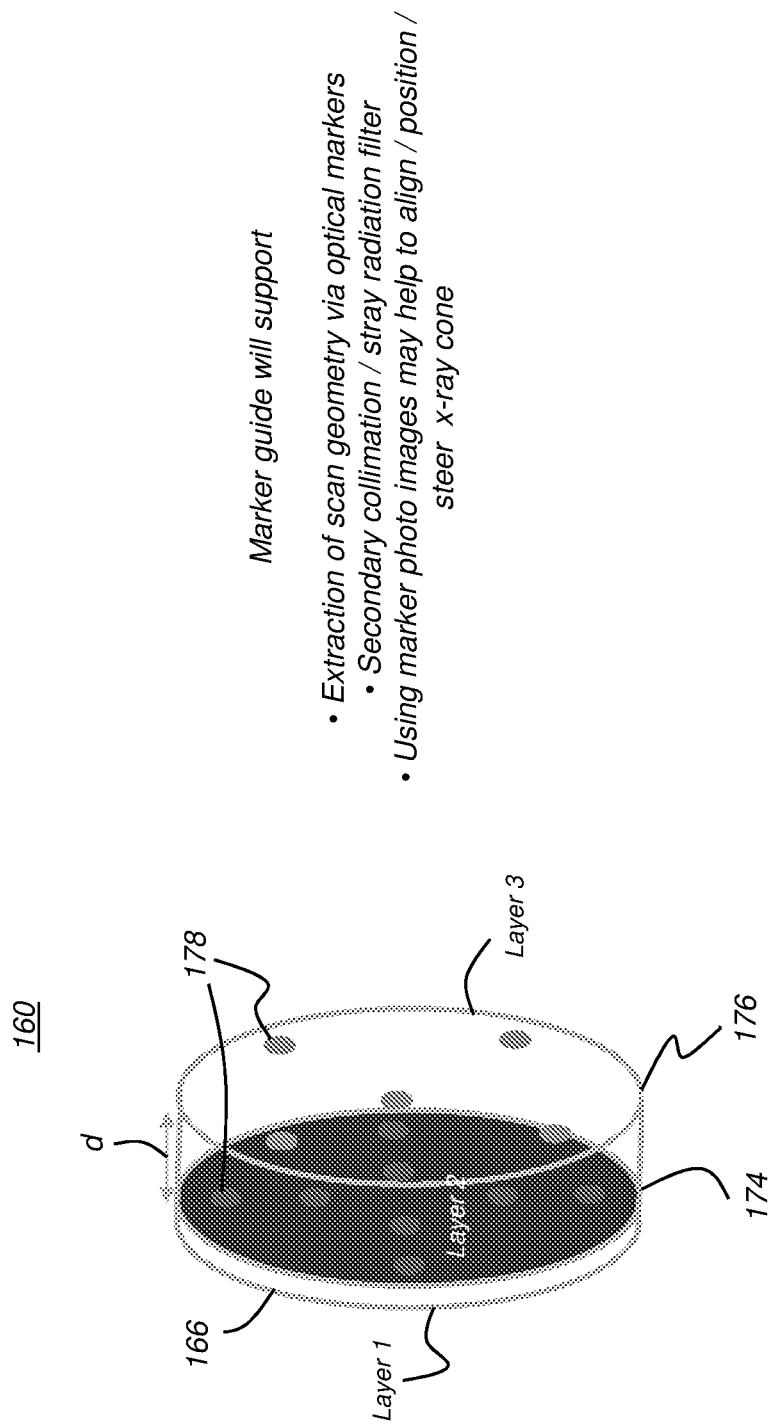
FIGS. 14A and 14B show the assembly and components of a marker guide for alignment according to an example embodiment according to the application.
Figure 14B:
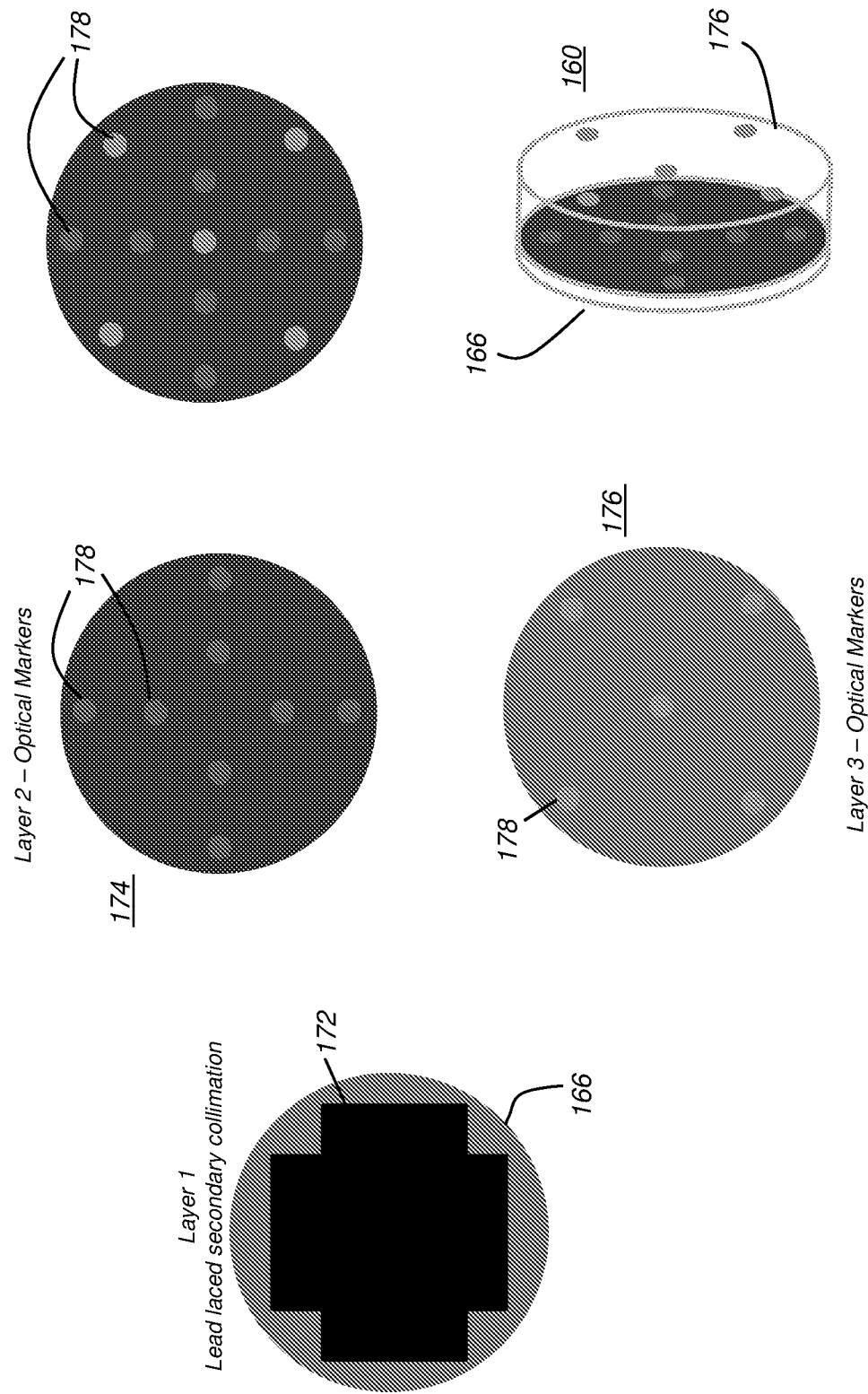

FIGS. 14A and 14B show the assembly and components of marker guide 160 according to example method and/or apparatus embodiments of the present disclosure. FIG. 14A shows example marker guide 160 as assembled. FIG. 14B shows layered components for forming marker guide 160. A collimation layer 166 serves as a secondary collimator for the incident x-ray beam, held substantially against the face of the patient and providing a window 172 framed with radio-opaque shielding for localized collimation. The shielding can be provided by lead-laced material, for example. Layer 2 174 and layer 3 176 provide optical markers 178 for assisting in extraction of scan geometry for alignment. Separation of layers 174, 176 by a distance d helps to facilitate alignment measurement. Markers 178 have an overlaid arrangement shown in FIG. 14B and can be sensed by camera 140, with the resulting image processed for obtaining alignment data. Markers 178 can be different shapes (e.g., non-symmetric), layers, 3D configurations, or colors to support alignment detection. One or more of markers 178 can alternately be radio-opaque.

Figure 15:
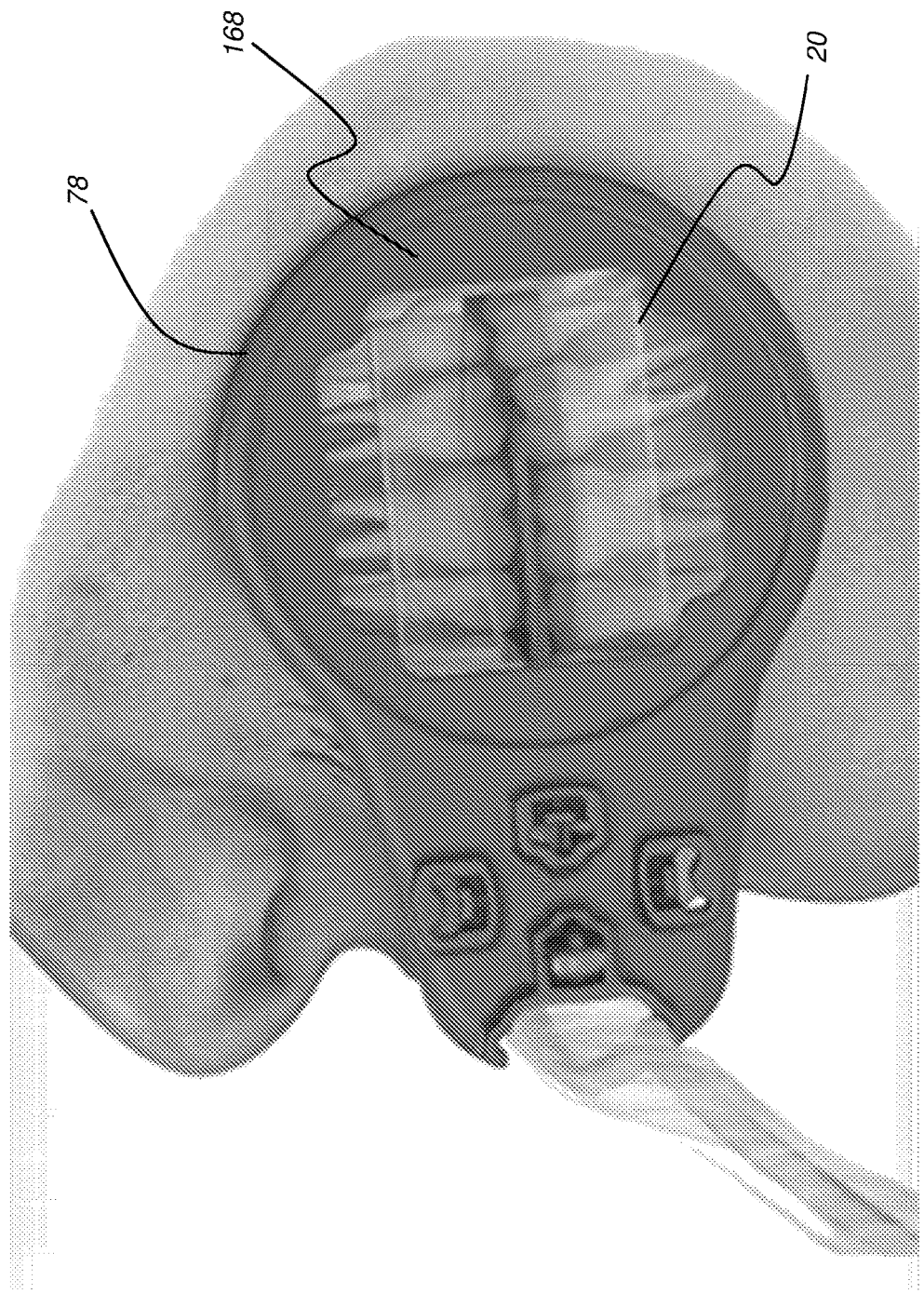
FIG. 15 shows position of a frame against the patient's face for alignment and collimation support.

Shown in position against the patient's face in FIG. 15, frame 78 has a support structure for proper alignment of collimation layer 166 of marker guide 160 relative to frame 78 (FIGS. 14A, 14B, 15). FIG. 15 also shows the position of intraoral detector 20 suitably positioned with respect to frame 78.

Figure 16:
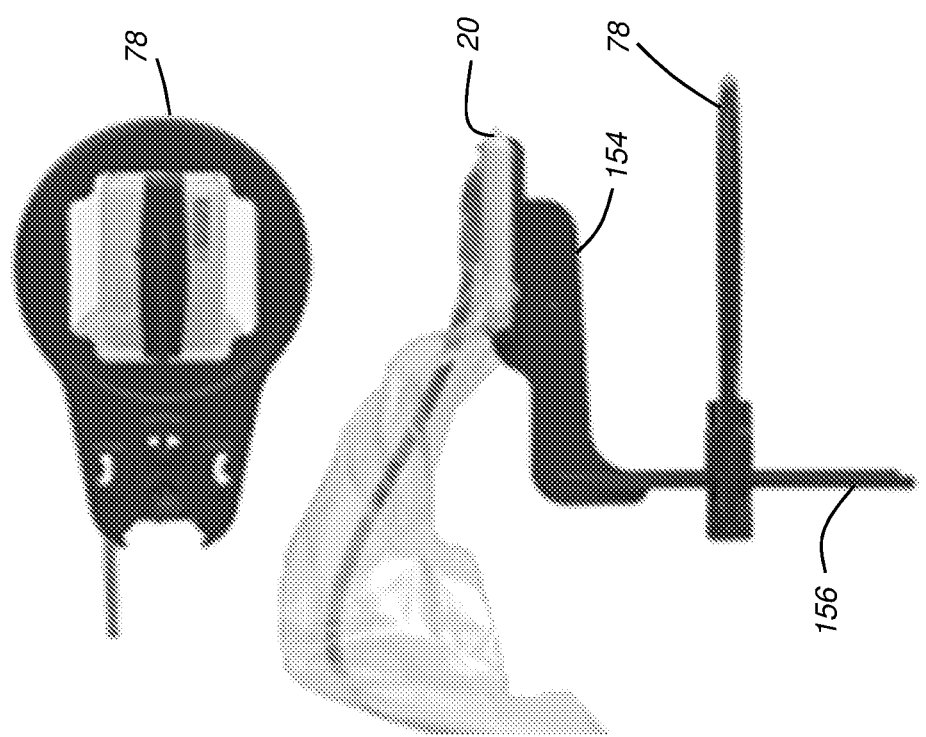
FIG. 16 shows side and top views of a frame for collimation and alignment and associated components.

FIG. 16 shows side and top views of frame 78 and associated components. A bite block 154 helps to stabilize the position of detector 20 within the mouth. An adjustable rod 156 allows positioning of the bite block 154 and detector 20 to suit the patient's comfort.

It should be noted that frame 78 and its associated marker components can be used with a single-source x-ray source 10 or with an array of x-ray sources, such as that provided using a Spindt-type field emitter-based x-ray source for example.

Figure 17:
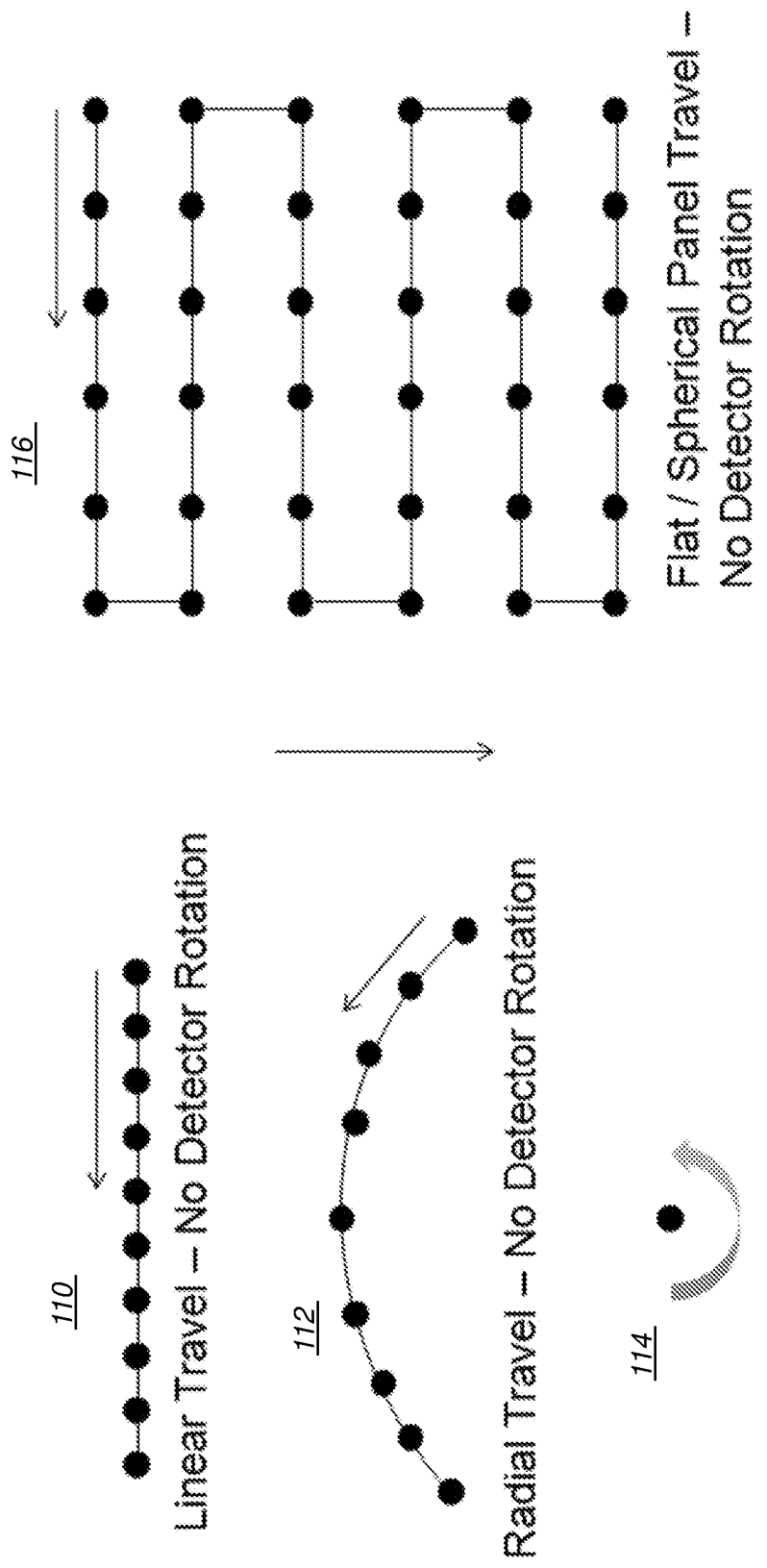
FIG. 17 is a schematic diagram showing example relative travel paths that can be traced relative to the imaged subject for tomosynthesis imaging.

The schematic diagram of FIG. 17 shows example relative travel paths that can be traced relative to the imaged subject for tomosynthesis imaging. A linear travel path 110 or radial travel path 112 can be provided without detector rotation. In travel path 114, the source remains in position while the director rotates. In travel path 116, flat or spherical source travel is provided, without detector rotation. For any of travel paths 110, 112, and 116, relative movement can be provided by successively energizing individual sources of an array, such as a CNT source array, for example.

It can be appreciated that control logic processor 26 obtains and stores both image data and positional information when performing tomosynthesis imaging. As each image is obtained, control logic processor 26 stores the image data and corresponding information about the relative spatial position of the energized x-ray source and detector 20. Position data and image data can be stored as part of the same data structure, such as in the image data file, or may be stored in separate data structures, such as in separate files or database locations. In one embodiment, control logic processor 26, then optionally provides information that indicates a recommended positional adjustment for the x-ray source for obtaining the next x-ray image at the next spatial position and the next angular orientation. This information on recommended positional adjustment can be provided in a number of ways, including displayed information on display 28 (FIG. 5), using an audible cue, or by providing graphical guidance to the operator in order to set up the next exposure, which can be in the form of projected image content and format, such as by projecting instructions or target information onto the cheek of the patient, for example. Relative positional information related to each image is stored in some form and used by image processing logic on control logic processor 26 in order to generate the volume image.

Use of Spindt-Type Field Emitter Based or Other Radiation Source Array

Figure 18:
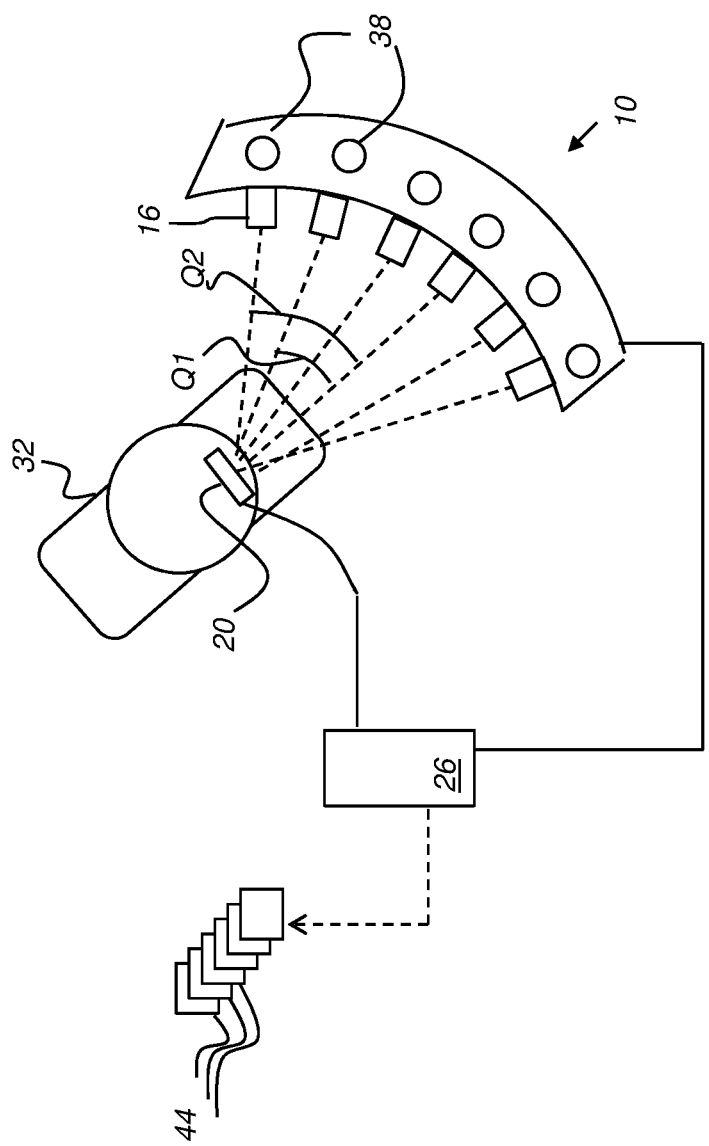
FIG. 18 is a schematic block diagram view that shows a Spindt-type field emitter based source or other x-ray source array for image acquisition.

The schematic diagram of FIG. 18 shows the use of a radiation source array as x-ray source 10. Each x-ray source 38 is from a cathode that utilizes Spindt-type field emitters. Using Spindt-type field emitter cathodes, the x-ray sources are stationary or relatively fixed in position with respect to each other within the array; the array itself moves as a single unit. This type of x-ray source is capable of rapid on/off switching on the order of microseconds. Other suitable x-ray sources can include paired pulsed conventional fluoro-capable thermionic sources that are spatially separated. These options provide sufficient x-ray fluence with short exposure times and simultaneously allow exposure sequences without overheating.

According to an example embodiment, each individual source 38 has its own collimator 16, as in the example embodiment shown in FIG. 18.

Alternate Concepts for Relative Movement

Data must be obtained in order to identify the spatial position of detector 20 and the relative spatial position of x-ray source 10 for each image.

According to the alternate example embodiment of FIG. 13B, described previously, x-ray source 10 is coupled to frame 78 by pivoting arm 192 that serves as a support and guide for source 10 movement in a curved or arcuate path. This arrangement allows source 10 movement over a well-defined angular track, simplifying design of transport apparatus for source 10 movement and further simplifying collimation design.

Figure 19:
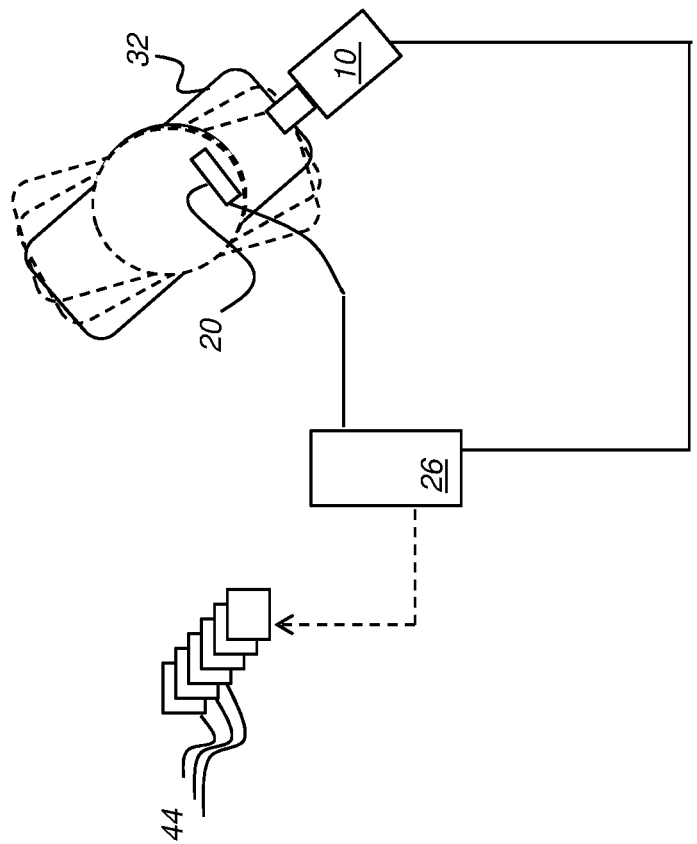
FIG. 19 is a schematic block diagram that shows an imaging pattern used for obtaining a volume image from a limited number of x-rays in an alternate example embodiment.

In the alternate example embodiment of FIG. 19, x-ray source 10 is fixed in place and patient 32 is rotated, such as by incrementally rotating a treatment chair for example, to shift from one exposure angular orientation to the next. Again, relative positional information for both detector 20 and x-ray source 10 must be established and stored for each component image by control logic processor 26 or a related processing device.

Image Acquisition Process

Figure 20:
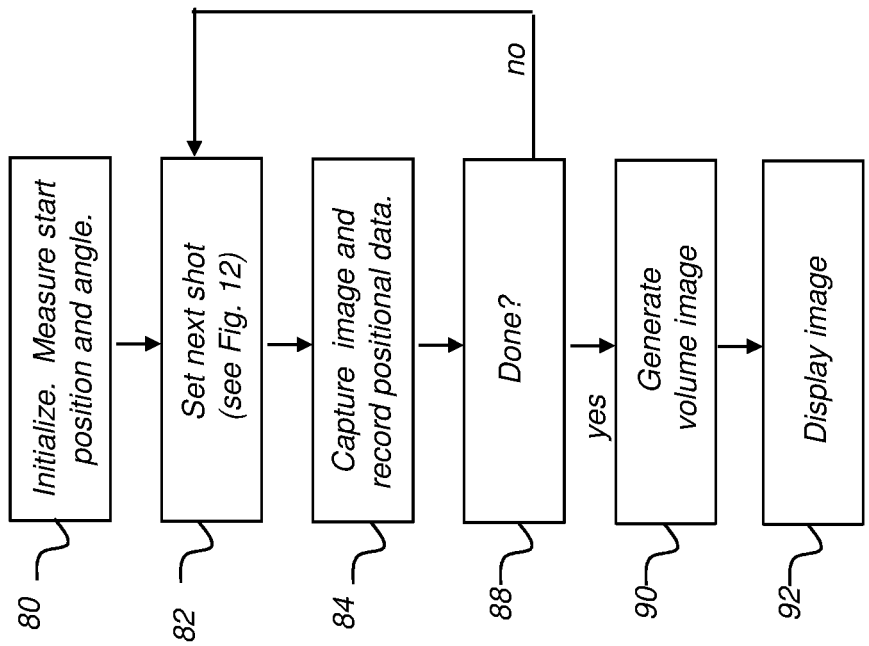
FIG. 20 is a logic flow diagram that shows a sequence for capturing x-ray images to generate a volume image.

The logic flow diagram of FIG. 20 shows a sequence of steps for obtaining a series of component images in one example embodiment. An initialization step 80 begins the sequence and obtains data on the initial start position and angle. In one embodiment, initialization step 80 also sets up or calculates the number of images to be obtained and, for each image, its corresponding exposure angle. This information may be fixed or variable, and may be calculated using control logic processor 26 or entered by the dentist or technician using setup software that is in communication with control logic processor 26. Detector 20 is securely positioned in the patient's mouth and the needed source-detector alignment is at least coarsely made by the technician. In a setup step 82, imaging apparatus 22 provides the needed image display, projected onto the face or head of the patient, to help guide alignment and aim of x-ray source 10, as was described earlier with reference to FIGS. 7A and 7B. In one embodiment, the image content that is projected onto a portion of the patient changes according to the relative accuracy of the angular orientation. This can be a change in color, intensity, blinking, or other attribute of the projected content. It should be noted that the display may provide a hint or suggestion of the best position for each subsequent radiographic image capture. However, it is important that the actual spatial position be accurately measured and recorded in order for proper execution of the limited-angle volume imaging algorithms.

Continuing with the logic flow of FIG. 20, each component image is obtained in an image capture step 84, and the image stored along with information about the actual measured spatial position and the angular orientation at which the exposure was obtained. A decision step 88 checks to determine whether or not all component images needed according to initialization step 80 have been obtained and loops back to setup step 82 when subsequent images are needed. At the conclusion of this processing for image capture, a volume image generation step 90 is executed in order to generate the resulting composite volume image obtained from this sequence. A display step 92 then displays the volume image that has been generated.

FIG. 21 is a block diagram showing spatial position and angular orientation associated with the image data for each component image 44 in the set of images that is obtained. In the example embodiment shown, a spatial position data field 50 and an angular orientation data field 52 are stored along with x-ray image data 54, such as by storing the measured position and angle geometry in a header portion of the x-ray image data file. Alternately, spatial position and angular orientation data can be separately stored, linked or otherwise associated with the image data. This information is needed for proper reconstruction of the volume image.

FIG. 22 is a logic flow diagram that shows optional system activity within image setup step 82 of FIG. 20 in preparation for each image capture in a sequence. A calculation step 60 uses position coordinate and angular orientation data from the x-ray system or stored with the previous image and calculates a next position and angular orientation for relative movement of x-ray source 10 and/or detector 20. An optional target projection step 62 then projects an image onto the patient, wherein the image is indicative of positional adjustment and angular adjustment that is needed between x-ray source 10 and detector 20 for obtaining a next x-ray image at the next spatial position and angular orientation. As noted earlier, the optional projected display can indicate the needed adjustment using color, blinking or other effects, numeric values, directional indicators or icons, such as an arrow, or other visual effects. Then, in a looping operation, a reassessment step 64 periodically readjusts the projected display according to measured changes in positional adjustment and angle that have been made by the technician. When adjustment is correct to within some predetermined tolerance, a correct adjustment display step 66 then executes, indicating that the adjustment is acceptable for obtaining the next image.

Given the information that is available on relative position when using the component arrangement shown in FIGS. 9A-11, an example embodiment of the present invention uses continual re-calculation and repeated checks of sensors and other position-sensing components for correction of, and adapting to, minor position changes and patient movement. With this arrangement, it is not necessary that detector 20 and x-ray source 10 have fixed, predetermined positions relative to each other or achieve precisely those positions calculated for the next image. However, in any case, detector 20 must have a fixed spatial position relative to the teeth or other objects being imaged. Programmed image processing logic can adapt to changes in position that are within a reasonable range of angles, for example. In one embodiment, one or more additional position sensors at fixed spatial positions are used to establish reference points for angular and positional orientation. In addition, automated detection and correction of patient motion artifacts can also be performed, using image processing techniques known to those skilled in the image acquisition arts.

The limited-angle volume image that is formed from two or more component x-ray images provides some measure of volume-related information for the tooth or other imaged structure. Advantageously, this is provided without the higher levels of exposure needed for full CBCT imaging and without the need for specialized CBCT gantry and related equipment. Positional information that is obtained using sensor 24 and detectable elements 30 is used by 3D image reconstruction algorithms to generate a corresponding volume image that includes a tooth or other feature and to populate voxels within that volume image with suitable data values. The volume image can be formed without requiring the complex filtered back-projection algorithms that are typically used for CBCT reconstruction, for example. Images obtained can be viewed on a conventional display monitor or may be viewed using a stereoscopic viewing apparatus, for example. The needed volume image can be generated dynamically according to a preferred viewing angle indicated by the practitioner, for example.

Variations in the Image Acquisition Sequence

According to an example embodiment according to the application, the image acquisition sequence can be varied in order to obtain one or more images under different conditions. For example, over a series of images taken under tomosynthesis conditions and angles, one or more images can be captured under different conditions, such as using settings typically applied for conventional 2D radiography imaging. This can be, for example, a central image in a sequence, such as the 10th or 11th image in a series of 20 tomosynthesis image captures. Different capture conditions, including exposure settings, binning, dual-energy and other parameters can be used for images acquired in this manner.

Where one or more images are obtained under different conditions, features such as higher fidelity and sharpness of these images can be used to improve image content for other images in the series.

Detector Binning

Binning methods can be used to help speed image acquisition. Binning groups sets of adjacent pixels together in order to speed image data access and data refresh cycles. Binning is typically done in a symmetrical pattern, such as 2×2 binning, 3×3 binning, etc. However, binning can also be performed in one direction, such as 2×1 binning, for example. Non-symmetric binning can be useful for volume imaging, with binning in the direction parallel to relative motion of the x-ray focal point different from binning in orthogonal directions.

Radioscopy

Radioscopy imaging methods, including fluoroscopy for example, obtain images of the subject in rapid succession and provide a continuous view of the subject that can have a video appearance. In radioscopy, volume reconstruction is not provided; instead, the sequence of acquired radiographic images displays. There is no relative movement between the x-ray source and the detector in radioscopy; the same source-to-detector geometry applies for each acquired image.

Radioscopy can be a useful tool for the practitioner, providing a progressive or "real-time" presentation of a region of interest, such as one or more teeth or a portion of a dental arch, for example. Radioscopic presentation can be combined with visualization software that indicates drill angles or other features that are helpful during a procedure. Radioscopy acquisition takes advantage of a high speed digital detector having good resolution.

In general, radioscopy has an acquisition time similar to that needed for tomosynthesis, but with somewhat longer x-ray exposure time. There can be a tradeoff of spatial resolution vs. dose for radioscopy acquisition.

Dual Energy Spectral Imaging

Certain example method and/or apparatus dual-energy imaging embodiments allow advantages of improved ability to analyze different types of tissue that are found in the imaged anatomy. Dual energy or multispectral imaging can be obtained using a conventional detector as well as using a photon-counting detector having multiple thresholds, as described previously with reference to FIG. 2B. Alternately, other detector arrangements can be used with a dual-energy x-ray source.

Dual energy (DE) imaging has been used as an alternative method for reducing noise content and differentiating various types of imaged anatomy and materials. In conventional DE imaging, low and high kVp exposures of the same anatomy follow each other in close succession, so that their results can readily be combined without requiring extensive registration techniques. This can help with subsequent segmentation of bone features, for example, allowing more accurate interpretation of the x-ray image content. For tomosynthesis and 3D volume imaging overall, such as provided by CBCT and CT apparatus, there can be significant advantages in providing dual-energy image content for reconstruction and subsequent analysis.

Dual energy tomosynthesis, with imaging content obtained using two different energy (or wavelength) bands that generate two different radiation spectral energy distributions, allows different structures to be reconstructed from the same imaged tissue.

Exposure technique settings can be varied from one projection image to the next during image acquisition.

Reconstruction

Control logic processor 26 or an associated processor or other computer used for image processing can execute any of a number of known techniques for limited-angle tomosynthesis reconstruction, familiar to those skilled in the 3D imaging arts. For example, some have described a number of reconstruction algorithms used to solve a similar type of problem in limited-angle mammographic imaging, including back-projection, algebraic reconstruction, and probabilistic techniques. The Siltanen et al. patent noted earlier describes a 3D reconstruction method from sparse 2D image data using modeling data for tooth structures. The Kalke application noted earlier describes another method for tooth image reconstruction using a frequency transform. Other reconstruction methods for 3D imaging could alternately be employed.

Among its advantages, a volume image can be formed for viewing image slices from different angles, depending on how much component image data is available. Where a sufficient number of component 2D projection images are obtained at different relative angles, the resulting volume image can be formed and displayed from multiple view angles, thus assisting the dental practitioner in making a more accurate diagnostic assessment of a tooth or other structure.

Presentation/GUI

The operator can have the capability to set up the operating mode of the imaging system using operator interface commands.

Figure 23:
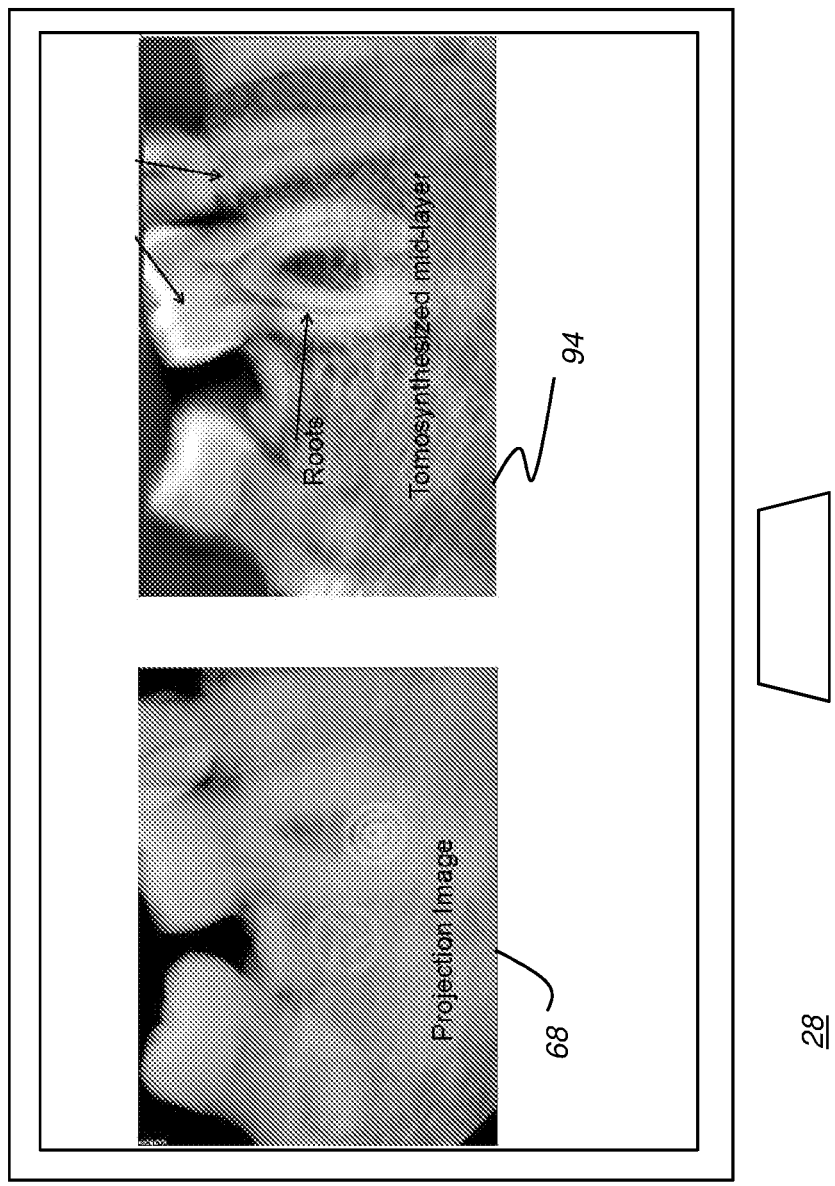
FIG. 23 shows a comparative display for a projection image and a tomosynthesis image slice.

According to an example embodiment according to the application, the operator interface on display 28 (FIG. 1) can show any subset of the projection images that have been obtained as part of the tomosynthesis series, as well as showing any suitable tomosynthesis slice from the reconstructed image data. FIG. 23 shows display 28 having a comparative display that shows a 2D projection image 68 alongside a corresponding tomosynthesis slice 94.

Geometric Calibration Using Spectral X-Ray Imaging

Used in conjunction with alignment methods and apparatus, as described previously, geometric calibration helps to provide improved accuracy and resolution for tomosynthesis reconstruction. Embodiments of the present disclosure provide a number of solutions for geometric calibration that utilize characteristics of spectral x-ray imaging. The methods for geometric calibration described herein can be suitable for chair-side dental tomosynthesis, as well as for other radiographic 2D imaging and 3D volume imaging applications, particularly where the detector is not mechanically coupled to the source and may not be visible during setup and imaging.

Geometric calibration calculations for volume imaging apparatus are familiar to those skilled in the volume image reconstruction art. Embodiments of the present disclosure are directed to identifying relative spatial coordinates of the x-ray source and detector; given this baseline data, computation of the needed spatial coordinates can be executed with sufficient accuracy for tomosynthesis or tomographic reconstruction.

Although existing methods for geometric calibration can provide accurate data on spatial positioning of the source with respect to the detector, there is still some need for improvement. The use of coupled mechanical devices for intraoral imaging can be awkward and uncomfortable for the patient. Where markers are used for geometric calibration, conflicts can occur between the need to view the image data without obstruction and the need to clearly and unambiguously detect the marker and distinguish the marker from other image content for deriving the needed geometric positioning or calibration data. In practice, either some of the image content used for diagnostics can be obscured, compromising diagnostic quality, or one or more of the positional markers can be difficult to detect, leading to erroneous or ambiguous measurement.

According to an alternate example embodiment of the present disclosure, geometric calibration is provided using spectral x-ray detection. As noted previously, two types of x-ray imaging architectures provide spectral information content and can be considered to form spectral x-ray systems:

(i) x-ray apparatus having dual-energy source or sources; and (ii) x-ray apparatus having a photon-counting detector, of either direct or indirect type.

For geometric calibration using spectral x-ray imaging, markers of a material having a distinctive attenuation response to x-rays at different wavelengths can be disposed, within a phantom, at known positions relative to each other and positioned between the x-ray source and the detector. The spectral imaging content can be obtained from a conventional detector with the dual energy source described as (i) above, or obtained from a photon-counting detector using a polychromatic x-ray source as in (ii) above. This spectral imaging content can be processed to provide separate images of either of two image types:

(a) anatomy image, usable for diagnostic/clinical purposes, either a 3D tomography image, a tomosynthesis (partial 3D) volume image or a (2D) projection image, wherein phantom markers are imperceptible or only barely visible in the anatomy image; and (b) marker image, that is, an image that clearly and unambiguously highlights or emphasizes the positions of phantom markers, but may have little or no anatomy image content.

Geometric calibration using spectral x-ray imaging begins with some initially known positional or spatial relationship between the markers within a phantom. The markers from the phantom, visible in the processed marker image ((b) as described above), can be used to calculate the remaining unknown spatial relationship data between source and detector and an overall coordinate system that is used for volume reconstruction.

Figure 24:
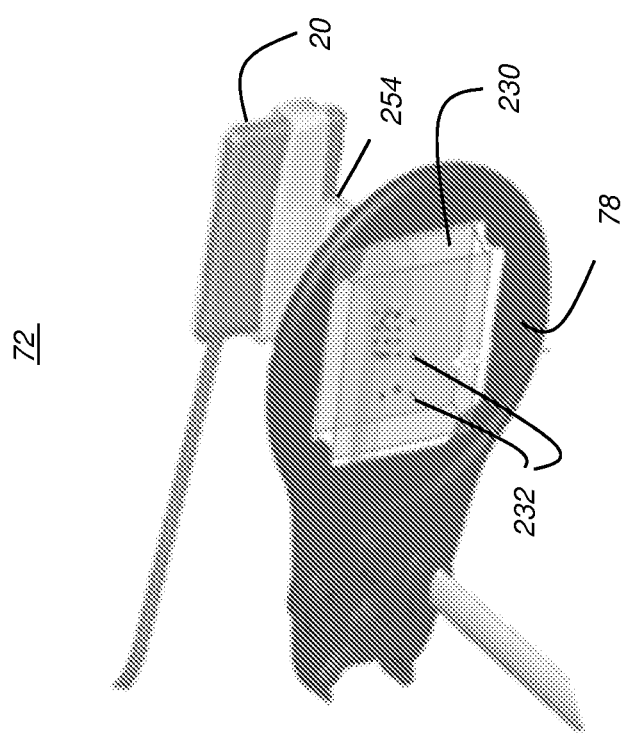
FIG. 24 is a schematic diagram that shows an arrangement with markers fixed in position relative to the detector.

Thus, for calibration setup, phantom markers are typically fixed in position relative to either the detector or the source. The schematic diagram of FIG. 24 shows an arrangement with markers fixed in position relative to the detector. Markers 232 in a phantom 230 are disposed within frame 78 of a holder 72 with a bite block 254. Holder 72 is used for alignment of the source with the detector 20. Alternate arrangements can include a phantom that is coupled to the teeth or other imaged object.

Figure 25:
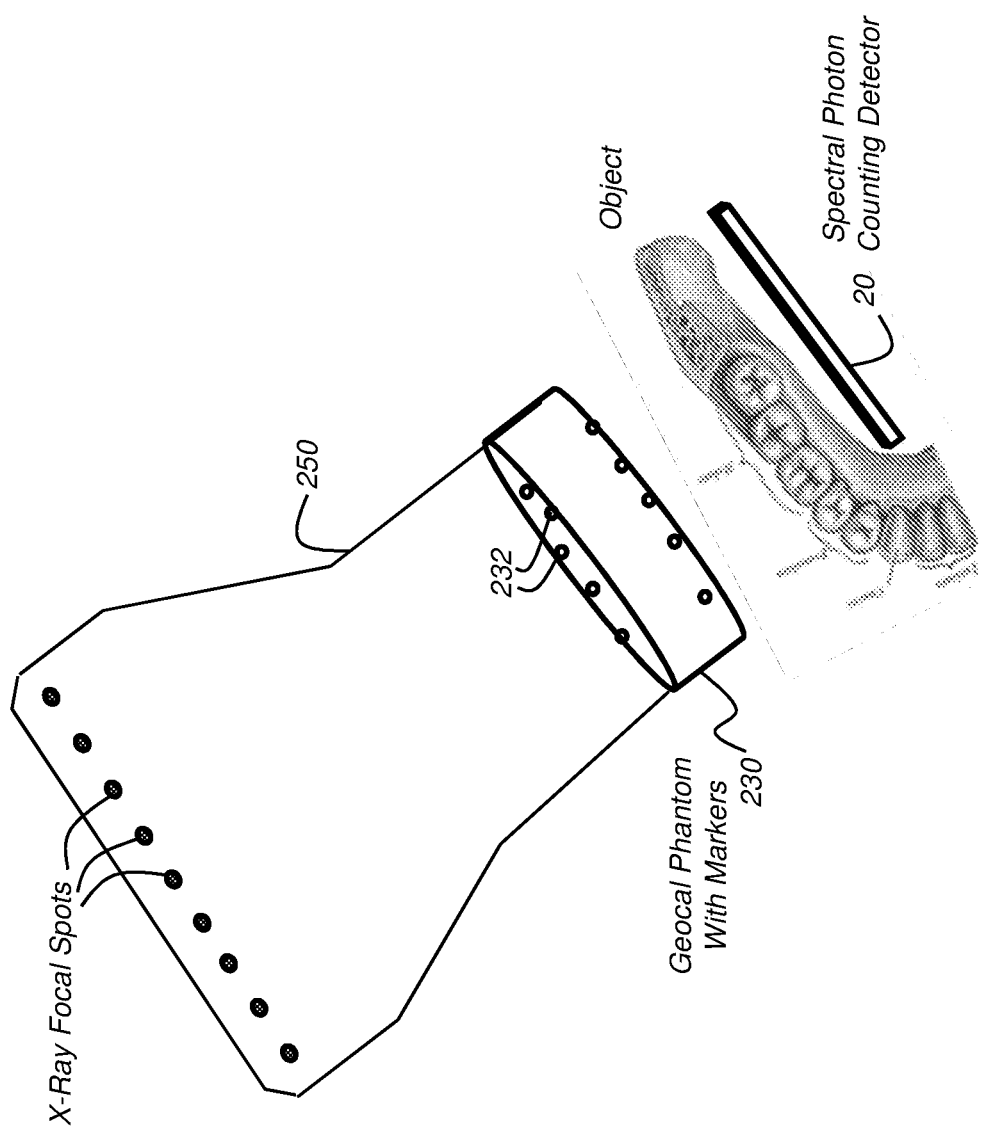
FIG. 25 is a schematic diagram showing an alternate arrangement in which markers of a phantom are fixed to the source.

FIG. 25 is a schematic diagram showing an alternate arrangement in which markers 232 of phantom 230 are fixed to the source, such as disposed within an x-ray hood 250.

It should be noted that the markers have a well-defined coordinate position relative to each other, whether or not their position relative to source or detector is known.

Embodiments of the present disclosure address the need for geometric calibration using markers and generating x-ray energy distributions with corresponding processing that allows reduced impact on image quality for the imaged anatomy as well as the capability to unambiguously indicate marker position. The example graphs of FIGS. 26A-26C show the spectral relationships that are used to generate the x-ray energy distributions that can then be combined and processed differently to alternately achieve the following:

(i) isolate marker content so that it can be enhanced to be more pronounced and unambiguous for geometric calibration purposes; and (ii) render the marker content to be less visible or even imperceptible to the viewer, thus allowing diagnostic use of the acquired image content.

To achieve these conflicting effects, an embodiment of the present disclosure generates two different x-ray energy distributions, wherein each distribution is a product of the number of photons or x-rays generated and the mass attenuation characteristics of marker and anatomy materials. Subsequent processing of these two different x-ray energy distributions then either enhances or suppresses marker content, using the sequence described following.

Figure 26A:
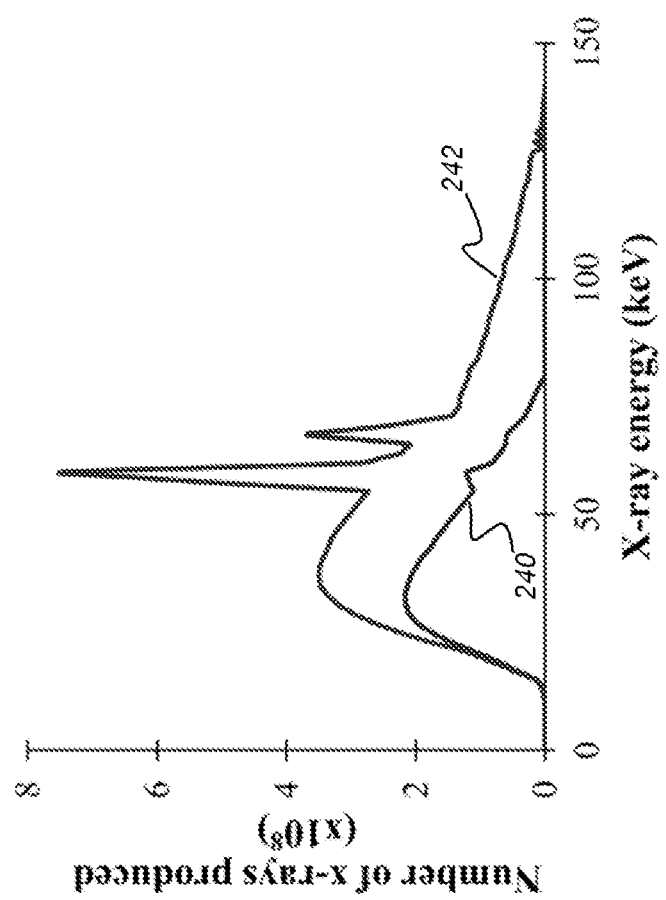
FIGS. 26A, 26B, and 26C are graphs showing x-ray energy and mass attenuation characteristics that are combined to define given x-ray energy distributions according to example embodiments of the present disclosure.
Figure 26B:
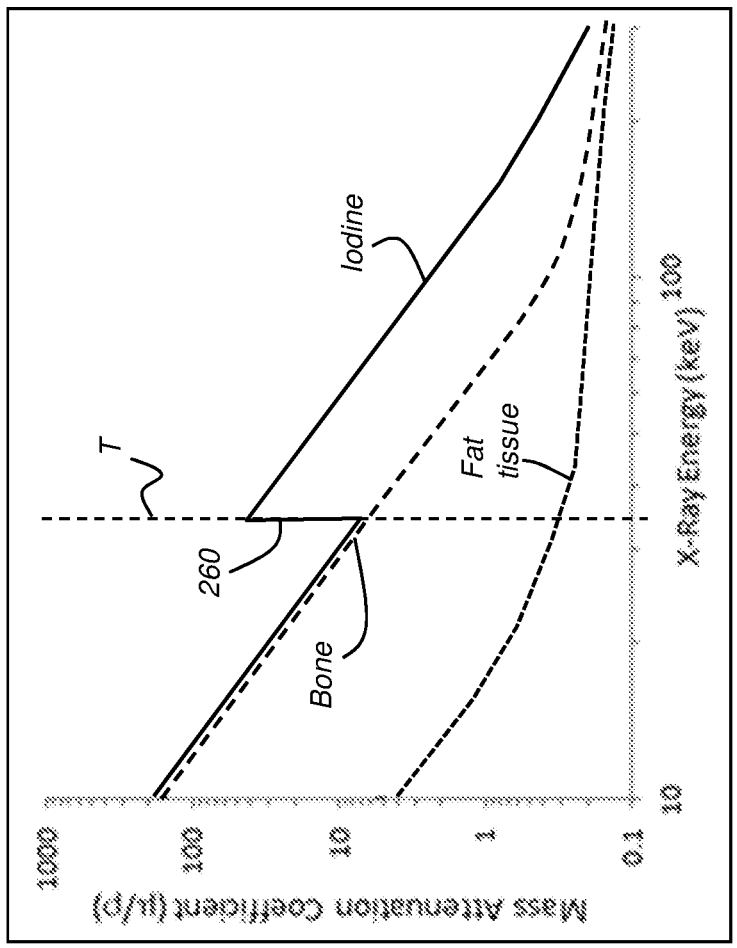
Figure 26C:
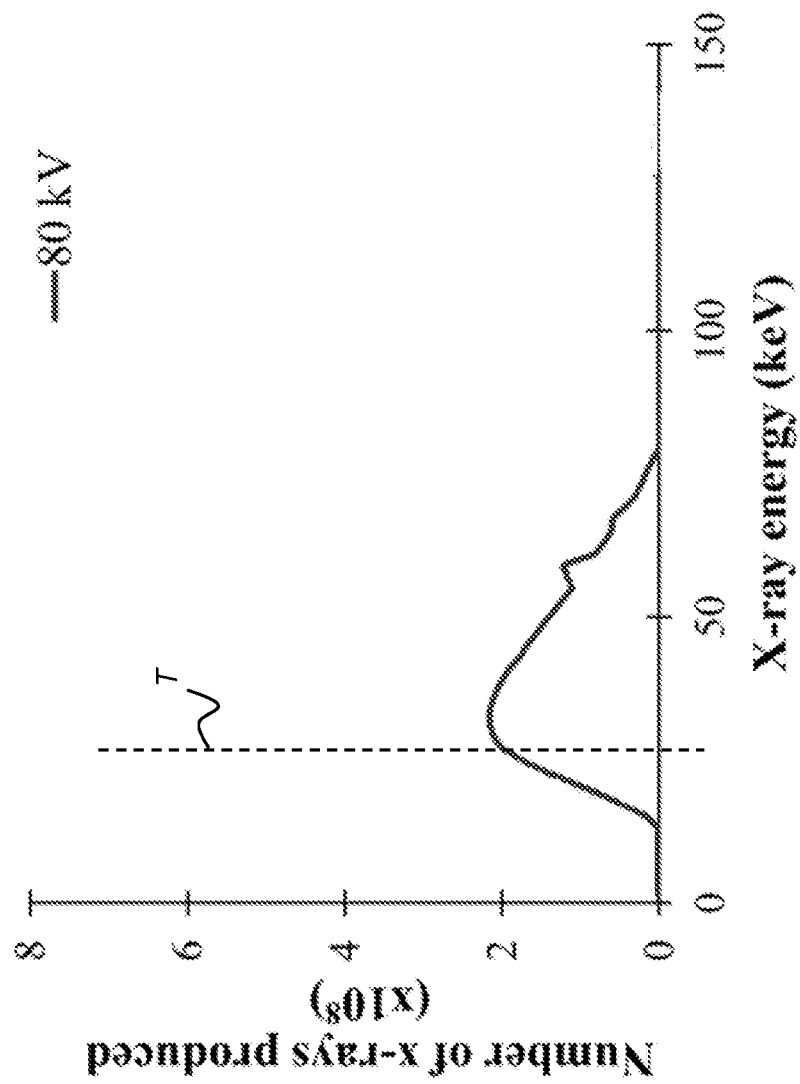

FIG. 26A shows energy characteristics for dual energy x-ray emission, in which two partially overlapping spectral wavelength bands of x-ray energy are sequentially generated and directed toward phantom 230 and the subject anatomy. Generated in rapid succession, the two x-ray images capture the subject in essentially the same position. FIG. 26A shows a lower energy characteristic curve 240 and a higher energy curve 242 for example dual energy emission. Each characteristic curve can be considered to represent a quantity of photons emitted over the different energy levels (keV) or spectral values, with the x-ray tube at two different kVp technique settings as shown.

FIG. 26B shows, in somewhat exaggerated form for clarity, characteristic mass attenuation coefficients μ for different tissue types, bone and soft tissue materials, and for one potential type of marker material, such as an iodine marker element. The x-ray absorption characteristics of a material provide a type of "signature" indicative of that material in the imaged subject. It is instructive to observe that there can be a noticeable discontinuity in the slope of the attenuation curve, known as a k-edge 260. K-edge 260 for iodine is noticeable in the 30-40 keV range (41-31 nm wavelength range). Other materials having a k-edge within the keV range used for most dental applications include Gadolinium, having a k-edge at 50.2 kV; Platinum, having a k-edge at 78.4 kV; Lead, having a k-edge at 88.0 kV; Gold, having a k-edge at 80.7 kV; and Silver, having a k-edge at 25.5 kV. The difference in attenuation between two materials can be most pronounced at or near the k-edge 260 for one of the materials, as shown.

To a first approximation, the x-ray energy distribution is represented by the effective mass attenuation $\mu_{\mathit{eff}}$ for a material, such as for bone in the present example. The effective mass attenuation $\mu_{\mathit{eff}}$ for a material can be considered as a summation or integral, over a portion of the energy spectrum E, of the product of the mass attenuation $\mu(E)$ curve of FIG. 26B and the spectral probability distribution $p(E)$ of x-ray energy as shown in the curve of FIG. 26A:

$$\mu_{\mathit{eff}} = \int \mu(E) p(E) dE$$

For each type of material (fatty tissue, bone, marker), different x-ray energy distributions relate directly to relationships of effective mass attenuation $\mu_{\mathit{eff}}$ can apply for lower and higher energy emission. For example, for soft tissue, values for Low energy (L) and High energy (H) emission energy distributions can be related as follows:

$$\mu_{\mathit{eff}}^L \approx \mu_{\mathit{eff}}^H$$

For bone material, the relationship for energy distributions changes to:

$$\mu_{\mathit{eff}}^L \gg \mu_{\mathit{eff}}^H$$

For marker material, the relationship changes to:

$$\mu_{\mathit{eff}}^L \ll \mu_{\mathit{eff}}^H$$

This relationship of x-ray energy distributions can be particularly pronounced in the vicinity of a k-edge, as shown in the example of FIG. 26B. In FIG. 26B, the iodine marker material has a k-edge within an energy range of the higher x-ray energy distribution. The marker material can have a k-edge within the energy range of either of the first or second x-ray energy distributions.

Thus, by suitable selection of spectral content and by comparison of the difference in effective attenuation coefficients according to the spectral characteristics, material components in the subject image can be distinguished from each other according to their respective x-ray energy distributions under given conditions. Embodiments of the present disclosure employ these differences on a pixel-by-pixel basis in order to selectively suppress or enhance marker content in the acquired image. For example, measuring the difference in energy distributions by subtraction or other combination, such as using a weighting, enables enhanced detection of materials using spectral characteristics. Prior knowledge of the marker material enables suppression of the marker image, such as in areas where the marker would otherwise obscure the anatomy.

The relationships of mass attenuation coefficients shown in FIG. 26B can also be used for single-energy emission when using a photon counting detector. FIG. 26C shows a characteristic distribution of spectral energy with a threshold value T that is used as the borderline value that distinguishes lower-energy photons (values below threshold T) from higher-energy photons (values above threshold T).

The capability to count photons below and above a defined energy threshold T, as described previously, allows detector 20 to differentiate between energy distributions obtained from irradiating the subject according to materials and provides added dimension to the image data that is provided as a result of each exposure. This capability, which has been described as multi-spectral or "color" x-ray imaging, enables information to be obtained about the material composition of each subject pixel.

As the attenuation curves of FIG. 26B suggest, there can be particular wavelengths (correspondingly, particular keV values) at which the attenuation factors for two different materials differ sufficiently from each other so that it is possible to identify the materials, from the x-ray image, according to distribution differences resulting from measured attenuation coefficients. Moreover, where photons of these different energy distributions can be differentiated from each other, it is possible to perform materials decomposition and thus identify one or both materials in the same pixel or voxel image element of the obtained image. This same basic attenuation behavior in response to radiation also allows some measure of capability for differentiating tissue types, for example.

As noted in the background section above, using markers facilitates accurate 3D reconstruction. Markers placed in the path of the x-ray beam can be imaged along with the imaged anatomy and can provide suitable positional information for geometric calibration purposes. However, calibration markers, because they are radio-opaque to some degree, can easily obscure portions of the imaged anatomy and can compromise the diagnostic value of the acquired image. This aspect of degrading image quality can particularly troublesome for the practitioner who may want to use both the 3D volume tomosynthesis reconstruction and the 2D projection images that were acquired as part of the tomosynthesis series. The 3D reconstruction algorithm can compensate somewhat for marker effects and may mitigate marker impact on the volume reconstruction. The 2D projection images, on the other hand, will clearly show radio-opaque markers and can block the view of portions of the imaged anatomy that are of interest. The use of markers with lower attenuation coefficients can be a poor solution, since the markers themselves may not be visible for some portions of the imaged anatomy.

An example embodiment of the present disclosure employs spectral x-ray imaging to address the problem of geometric calibration for tomosynthesis imaging using markers. Example embodiments of the present disclosure can employ a phantom having a set of markers 232 as described previously in FIGS. 24 and 25.

Preferably, markers are disposed within the imaging area of the detector, disposed at or near the center of the imaging area or arranged symmetrically about the center of the imaging area. With this centered arrangement, markers lie within the imaging area in each 2D projection image.

Markers 232 can be formed of any of a number of suitable materials for intraoral use. The marker material can have an attenuation coefficient $\mu_m$ that is lower than conventional markers. Non-toxic materials that can be appropriate for intraoral imaging can include chromium steel, ceramic, tungsten carbide, and gold, for example. Markers 232 can be spherical. A suitable size range for tomosynthesis imaging is 0.5 mm diameter. Other sizes and shapes can be used as desired.

According to an example embodiment of the present disclosure, other materials that are radio-opaque, particularly those with atomic numbers of 45 or below, can be used. Example materials of this type include chromium steel (with atomic number 26) and ZrO2 ceramic material (with atomic number 40). Materials having opacity in this range tend to generate correspondingly lower intensity imaging artifacts than do materials that exhibit higher attenuation to radiation.

Markers 232 can be iodine or other material having a distinctive k-edge 260 within the x-ray energy range, as shown in the simplified graph of FIG. 26B. As noted previously, there can be a noticeable discontinuity in the slope of the attenuation curve for a k-edge 260. K-edge 260 for iodine is noticeable in the 30-40 keV range (41-31 nm wavelength range). Other materials having a k-edge within the keV range typically used for dental applications can include Gadolinium, Platinum, Lead, Gold; and Silver.

Compared with conventional marker approaches that use spherical BBs or other particles of high-attenuation materials, the marker materials that are used in the Applicant's process can have reduced attenuation, so that there is reduced impact on the imaged anatomy in 2D projection images. In addition, according to the example methods described herein, processing of the acquired images can be provided that accentuates marker 232 content, to reduce ambiguous or confusing image content and more clearly show marker position.

The markers appear in each 2D projection image of the tomosynthesis series. Given the well-defined marker placement on the detector and knowing the source path of the incident radiation for tomosynthesis, the acquired 2D projection images can allow the imaging system to be geometrically calibrated for accurate reconstruction.

Image processing techniques can be applied in order to compensate for marker 232 appearance and obstruction caused by the marker. Well-known techniques such as in-painting and interpolation can be used to suppress or remove the marker(s) from one or more of the projection images, thereby helping to minimize or eliminate metal artifacts, for example.

Thus, according to an example embodiment of the present disclosure, there is provided a radiographic volume imaging apparatus having a) an x-ray source and detector that are disposed to define a radiation path through a subject and through a calibration phantom and that are configured to generate 2D projection image data having at least first and second x-ray spectral energy distributions, wherein the calibration phantom has a plurality of radio-opaque markers formed of a marker material. The imaging apparatus further has a control logic processor that is configured to execute programmed instructions for: (i) obtaining the 2D projection image data from the detector; (ii) calculating source-to-detector geometry of the imaging apparatus corresponding to the acquired 2D projection image data of the calibration phantom for the first and second x-ray energy distributions; and (iii) reconstructing a 3D volume image of the subject according to acquired anatomy image data from the subject and source-to-detector geometry within the plurality of 2D projection images. A display is in signal communication with the control logic processor and is configured to display one or more portions of the reconstructed 3D volume image.

Figure 27:
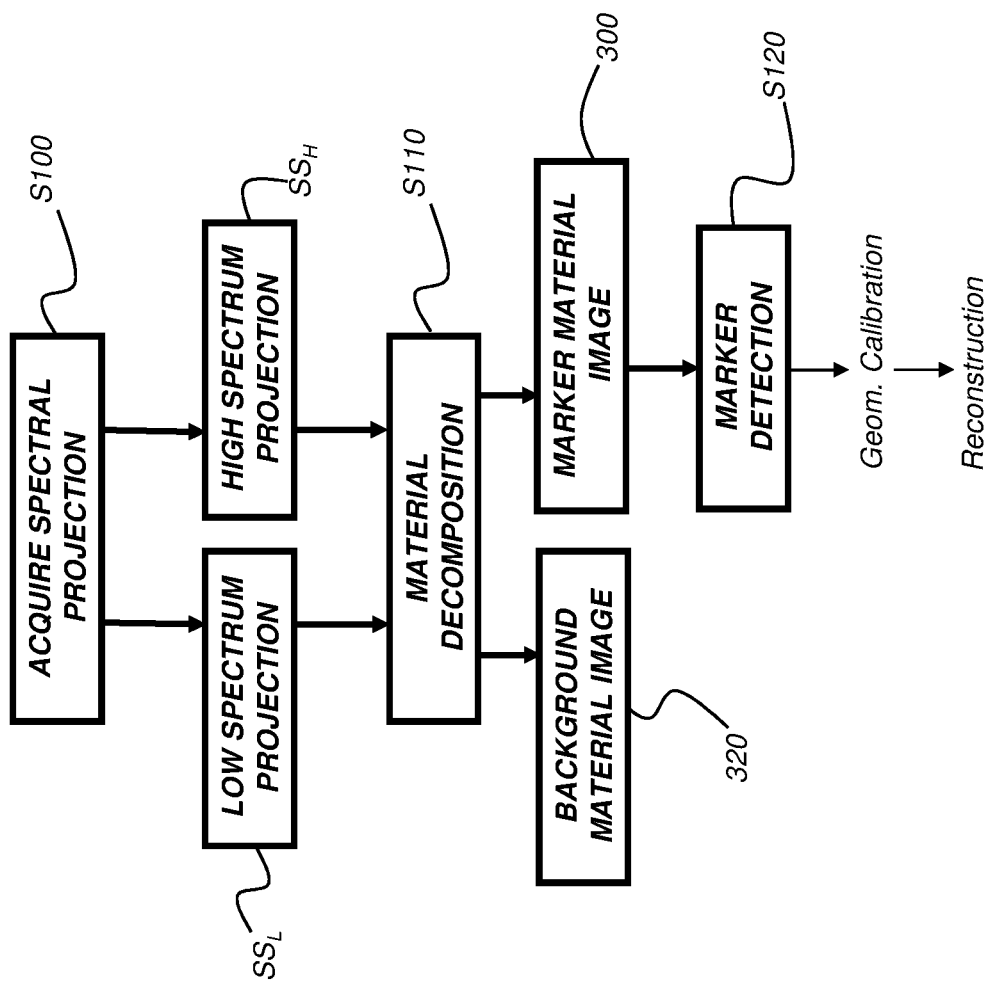
FIG. 27 is a logic flow diagram that shows a sequence for providing marker and anatomy 2D images from a single 2D projection image that is obtained using a spectral x-ray imaging system.

The example methods herein employ the principles described with reference to FIGS. 26A-26C to use spectral imaging for geometric calibration of the tomosynthesis or other volume imaging system. The logic flow diagram of FIG. 27 shows a sequence for providing both marker and anatomy content from 2D projection image content that is obtained using a spectral x-ray imaging system with either dual energy source or photon counting detector, as described above.

In an acquisition step S100, a spectral x-ray projection image is obtained. As has been shown with reference to FIGS. 26A, 26B, and 26C, the spectral x-ray projection image can be acquired either from a dual-energy source using a standard x-ray detector or from a polychromatic x-ray source using a photon counting detector. The spectral image content is thus partitioned according to spectral content (photon energy, in units of keV).

At a minimum, for photon counting detectors, the spectral image data can be part of a low spectrum band or subset $SS_L$, with keV energy below a predetermined threshold T, or part of a high spectrum band or subset $SS_H$, with keV energy above threshold T. Various combinations of the low and high spectra response can accentuate marker 232 content or reduce or eliminate marker content.

A threshold x-ray energy value T is determined as the boundary between a lower spectrum band and a higher spectrum band. In practice, the threshold value is taken at a keV value (or alternately considered, at a wavelength nm value) wherein a difference between the attenuation coefficient value of the marker 232 material $\mu_m$ and the attenuation coefficient value of the imaged anatomy can be readily measured. The threshold value T shown in FIG. 26C, taken along or near a k-edge 260, can be appropriate for dividing between low and high bands, since values at or near value T can be pronouncedly different for the markers vs. for the anatomy.

Continuing with the FIG. 27 sequence, a material decomposition step S110 then processes the subsets $SS_L$, $SS_H$ of spectral image data to generate image content of two different types:
  (i) marker material image content 300 that can be processed to clearly and distinctly show the marker arrangement. Marker material image content 300 utilizes the attenuation characteristics for the marker material to isolate the marker content 300 from background anatomy. The marker material image content 300 can include little or no useful anatomy content, but relates primarily to spatial positions of the marker material(s) in the image content. With further processing, unambiguous marker positions can be detected, allowing ready identification of each marker within the image frame in a subsequent marker detection step S120 that follows. Given a known phantom position relative to either the source or the detector and a marker image that clearly shows the relative spatial location of phantom markers 232 by position at the image plane, there is sufficient information for calculations that provide geometric calibration, using geometric methods well known to those skilled in the art.

(ii) a background image 320 that shows the imaged anatomy, with sufficient contrast and resolution for diagnostic functions.

Figure 28A:
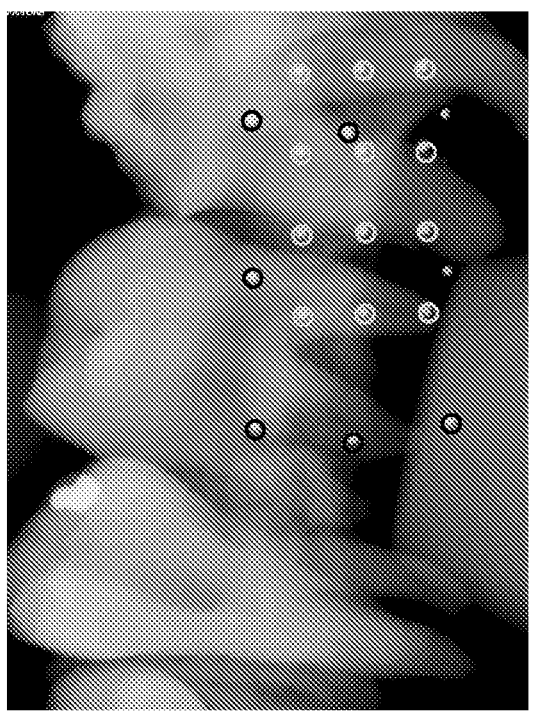
FIGS. 28A-28C show, in simulated form, results of image processing for marker detection within a 2D projection image for tomosynthesis imaging according to an example embodiment of the present disclosure.
Figure 28B:
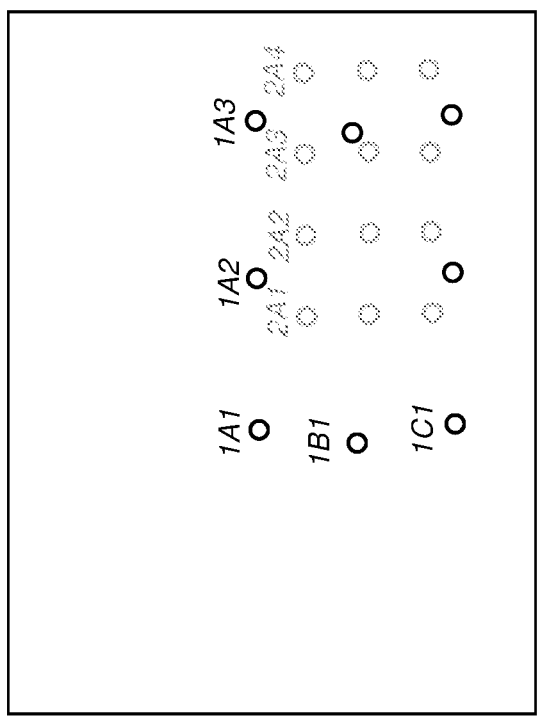
Figure 28C:
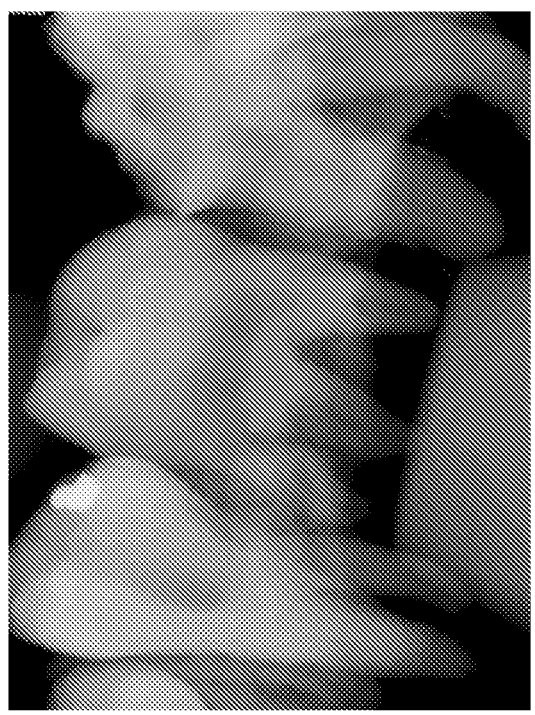

FIGS. 28A-28C show, in simulated form, results of image processing for marker 232 detection within a 2D projection image for tomosynthesis imaging according to an example embodiment of the present disclosure. FIG. 28A shows an acquired 2D projection image having a conventional set of markers 232 for geometric calibration. In this example, markers are spherical or BB-type markers 232, arranged along two planes that extend orthogonally with respect to the beam direction. Markers 232 in each plane can be differentiated by shape, density, or other factor. The relative shift between marker 232 positions in the image corresponds to the relative spatial positions of source and detector. It can be readily appreciated that this conventional marker image content blocks portions of the diagnostic image content.

FIG. 28B shows an example marker image 310. This image may or may not be generated; however, FIG. 28B shows how markers 2332 can be accentuated using the methods described herein. Optional labels can be provided to identify individual markers 232, as in the example labels 1A1-1C1, 2A1-2A4 shown. Marker image 310 is obtained by processing, such as in marker detection step S120 of FIG. 27. When using spectral x-ray data, the difference between low spectrum data and high spectrum data, with proper threshold value selection, is useful for calculating marker 232 position in the acquired data. Thus, with reference to the FIG. 27 sequence, processing methods for forming a marker image 310 typically obtain a weighted difference between the low spectrum projection $SS_L$ and high spectrum projection $SS_H$ in material decomposition step S110.

FIG. 28C shows an example background image 320 corresponding to the marker image 310 given in FIG. 28B. For the observer, markers can be imperceptible, or only barely perceptible, against the anatomy content shown in the background image. Material decomposition step S110 can provide additional processing that subtracts or otherwise removes marker image 310 from the full image obtained from the combined how and high spectrum projections. This effectively allows removal of marker content from background material image 320.

Following the sequence outlined in FIG. 27, geometric calibration data has been generated for each of the 2D projection images in the tomosynthesis series. Subsequent reconstruction processing can then generate 3D volume image content using the set of background material images along with the associated calibration marker data.

The present invention has been described in detail with particular reference to presently understood example embodiments, but it should be understood that variations and modifications can be affected within the spirit and scope of the invention.

For example, control logic processor 26 can be any of a number of types of logic processing device, including a computer or computer workstation, a dedicated host processor, a microprocessor, logic array, or other device that executes stored program logic instructions.

The presently disclosed example embodiments are, therefore, considered in all respects to be illustrative and not restrictive. The scope of the invention is indicated by the appended claims, and all changes that come within the meaning and range of equivalents thereof are intended to be embraced therein.

Consistent with at least one example embodiment, example methods/apparatus can use a computer program with stored instructions that perform on image data that is accessed from an electronic memory. As can be appreciated by those skilled in the image processing arts, a computer program of an example embodiment herein can be utilized by a suitable, general-purpose computer system, such as a personal computer or workstation. However, many other types of computer systems can be used to execute the computer program of described example embodiments, including an arrangement of one or networked processors, for example.

A computer program for performing methods of certain example embodiments described herein may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. Computer programs for performing methods of described example embodiments may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the application, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that can be directly associated with a display device and is periodically refreshed as needed in order to provide displayed data. This temporary storage buffer can also be considered to be a memory, as the term is used in the application. Memory is also used as the data workspace for executing and storing intermediate and final results of calculations and other processing. Computer-accessible memory can be volatile, non-volatile, or a hybrid combination of volatile and non-volatile types.

It will be understood that computer program products for example embodiments herein may make use of various image manipulation algorithms and/or processes that are well known. It will be further understood that example computer program product embodiments herein may embody algorithms and/or processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the application, are not specifically shown or described herein and may be selected from such algorithms, systems, hardware, components and elements known in the art.

Example embodiments according to the application can include various features described herein (individually or in combination).

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations/example embodiments, such feature can be combined with one or more other features of the other implementations/example embodiments as can be desired and advantageous for any given or particular function. The term "a" or "at least one of" is used to mean one or more of the listed items can be selected. The term "about" indicates that the value listed can be somewhat altered, as long as the alteration does not result in nonconformance of the process or structure to the illustrated example embodiment. Other embodiments of the invention will be apparent to those skilled in the art from consideration of the specification and practice of the invention disclosed herein. It is intended that the specification and example embodiments be considered as examples only, with a true scope and spirit of the invention being indicated by the following claims.

What is claimed is:

1. A method for geometric calibration of a volume imaging apparatus, the method comprising:
   (a) disposing a calibration phantom in a radiation path that includes a subject positioned between an x-ray source and a detector, wherein the phantom has a plurality of radio-opaque markers formed of a marker material;
   (b) in a repeated sequence, at each of a plurality of relative positional relationships of the x-ray source to the detector:
      (i) acquiring 2D projection image data for the subject and the phantom, wherein the 2D projection image data distinguishes at least first and second x-ray energy distributions;
      (ii) calculating source-to-detector geometry of the imaging apparatus corresponding to the acquired 2D projection image data for the first and second x-ray energy distributions; and
   (c) reconstructing and displaying a 3D volume image of the subject according to acquired anatomy image data from the subject and calculated source-to-detector geometry within the 2D projection image data.

2. The method of claim 1, wherein the volume imaging apparatus is a tomosynthesis imaging apparatus.

3. The method of claim 1, further comprising forming at least one 2D anatomy image of the subject according to combined data of the first and second energy distributions.

4. The method of claim 3, wherein forming the at least one 2D anatomy image of the subject further comprises suppressing radio-opaque marker content from the 2D anatomy image and displaying the 2D anatomy image.

5. The method of claim 1, wherein reconstructing the 3D volume image further comprises suppressing radio-opaque marker content from the 2D projection images.

6. The method of claim 1, further comprising forming an image having enhanced marker content according to material decomposition of the 2D projection image data.

7. The method of claim 1, wherein acquiring the 2D projection data comprises exposing the subject using a photon-counting detector.

8. The method of claim 1, wherein acquiring the 2D projection data comprises exposing the subject using a dual-energy x-ray source.

9. The method of claim 1, wherein the marker material is taken from a group including iodine, gadolinium, platinum, lead, gold, and silver.

10. The method of claim 1, wherein the phantom is coupled to the x-ray source or to the detector.

11. The method of claim 1, wherein the marker material has a k-edge within an energy range of either of the first or second x-ray energy distributions.

12. A method for radiographic imaging comprising:
   (a) disposing a calibration phantom in a radiation path that includes a subject positioned between an x-ray source and a detector, wherein the phantom has a plurality of radio-opaque phantom markers formed of a marker material;
   (b) acquiring 2D projection image data of the subject and the phantom, wherein the 2D projection image data distinguishes at least first and second x-ray energy distributions;
   (c) identifying relative spatial locations of the phantom markers in the 2D projection image data;
   (d) performing geometric calibration using the identified spatial locations of the phantom markers; and
   (e) forming and displaying a 2D projection image that shows anatomy of the subject and suppresses the phantom markers, wherein suppressing the phantom markers is based on the identified spatial locations of the phantom markers and the at least first and second x-ray energy distributions of the 2D projection image data.

13. The method of claim 12, wherein forming and displaying the 2D projection image further comprises using a weighted subtraction.

14. The method of claim 12, wherein acquiring the 2D projection image data comprises acquiring the 2D projection image data for the subject using a photon-counting detector.

15. The method of claim 12, wherein acquiring the 2D projection data comprises exposing the subject using a dual-energy x-ray source.

16. The method of claim 12, wherein the marker material is taken from a group including iodine, gadolinium, platinum, lead, gold, and silver.

17. The method of claim 12, wherein the phantom is coupled to the x-ray source or to the detector.

18. A radiographic volume imaging apparatus comprising:
   (a) an x-ray source and detector that are disposed to define a radiation path through a subject and through a calibration phantom, wherein the x-ray source and detector are configured to generate 2D projection image data having at least first and second x-ray spectral energy distributions, and wherein the calibration phantom has a plurality of radio-opaque markers formed of a marker material;
   (b) a control logic processor that is configured to execute programmed instructions for:
      (i) obtaining the 2D projection image data from the detector;
      (ii) calculating source-to-detector geometry of the imaging apparatus corresponding to the acquired 2D projection image data of the calibration phantom for the first and second x-ray energy distributions;
      (iii) reconstructing a 3D volume image of the subject according to acquired anatomy image data from the subject and the calculated source-to-detector geometry; and
   (c) a display that is in signal communication with the control logic processor and is configured to display one or more portions of the reconstructed 3D volume image.

19. The apparatus of claim 18, wherein the volume imaging apparatus is a tomosynthesis imaging apparatus.

20. The apparatus of claim 19, wherein the marker material has a k-edge within an energy range of either of the first or second x-ray spectral energy distributions.

* * * * *